United States Patent
Throckmorton et al.

(10) Patent No.: US 10,350,341 B2
(45) Date of Patent: Jul. 16, 2019

(54) IMPELLERS, BLOOD PUMPS, AND METHODS OF TREATING A SUBJECT

(71) Applicants: Amy Throckmorton, Cherry Hill, NJ (US); Steven Chopski, Philadelphia, PA (US)

(72) Inventors: Amy Throckmorton, Cherry Hill, NJ (US); Steven Chopski, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 273 days.

(21) Appl. No.: 15/073,739

(22) Filed: Mar. 18, 2016

(65) Prior Publication Data

US 2016/0271309 A1    Sep. 22, 2016

Related U.S. Application Data

(60) Provisional application No. 62/136,382, filed on Mar. 20, 2015.

(51) Int. Cl.
*A61M 1/10* (2006.01)
*A61M 1/12* (2006.01)
(Continued)

(52) U.S. Cl.
CPC .......... *A61M 1/122* (2014.02); *A61M 1/1012* (2014.02); *A61M 1/1024* (2014.02);
(Continued)

(58) Field of Classification Search
CPC ........ F04D 3/02; F04D 29/026; F04D 29/043; F04D 29/181; A61M 1/101;
(Continued)

(56) References Cited

U.S. PATENT DOCUMENTS

| 4,468,130 A | 8/1984 | Weetman |
| 4,627,791 A | 12/1986 | Marshall |

(Continued)

FOREIGN PATENT DOCUMENTS

| WO | WO 2005030296 A2 | 4/2005 |
| WO | WO 2009073037 A1 | 6/2009 |

(Continued)

OTHER PUBLICATIONS

Bhaysar, S. S., et al., "Intravascular mechanical cavopulmonary assistance for patients with failing Fontan physiology", Artif. Organs 33(11):977-87, 2009.

(Continued)

*Primary Examiner* — Igor Kershteyn
*Assistant Examiner* — Christopher R Legendre
(74) *Attorney, Agent, or Firm* — Saul Ewing Arnstein & Lehr LLP; Kathryn Doyle; Brian R. Landry

(57) ABSTRACT

One embodiment of the invention provides a variable pitch impeller for a blood pump. The variable pitch impeller includes: a flexible polymer defining a plurality of blades extending from a first end to a second end, the blades having a resting non-zero pitch; an external shaft coupled to a first end of the flexible polymer; and an internal shaft received within the external shaft and coupled to the second end of the flexible polymer. The internal shaft and the external shaft are rotatable with respect to each other to achieve a blade pitch between about 0.0001° and about 2,880°.

16 Claims, 26 Drawing Sheets

(51) Int. Cl.
 F04D 3/02 (2006.01)
 F04D 29/02 (2006.01)
 F04D 29/18 (2006.01)
 F04D 29/043 (2006.01)

(52) U.S. Cl.
 CPC .............. *A61M 1/1034* (2014.02); *F04D 3/02* (2013.01); *F04D 29/026* (2013.01); *F04D 29/043* (2013.01); *F04D 29/181* (2013.01); *A61M 1/101* (2013.01); *A61M 1/1086* (2013.01); *A61M 1/125* (2014.02); *A61M 2205/0266* (2013.01); *A61M 2205/3334* (2013.01)

(58) Field of Classification Search
 CPC .............. A61M 1/1012; A61M 1/1024; A61M 1/1034; A61M 1/1086; A61M 1/122; A61M 1/125
 See application file for complete search history.

(56) References Cited

U.S. PATENT DOCUMENTS

| | | | |
|---|---|---|---|
| 5,100,423 A * | 3/1992 | Fearnot | A61B 17/2202 604/22 |
| 5,347,190 A | 9/1994 | Lewis | |
| 5,355,042 A | 10/1994 | Lewis | |
| 5,480,382 A * | 1/1996 | Hammerslag | A61M 25/0053 600/585 |
| 5,749,855 A | 5/1998 | Reitan | |
| 5,972,019 A * | 10/1999 | Engelson | A61B 17/221 606/159 |
| 6,074,180 A | 6/2000 | Khanwilkar | |
| 6,351,048 B1 | 2/2002 | Schob | |
| 6,394,769 B1 | 5/2002 | Beamson | |
| 6,533,716 B1 | 3/2003 | Schmitz-Rode | |
| 6,595,762 B2 | 7/2003 | Khanwilkar | |
| 6,660,014 B2 * | 12/2003 | Demarais | A61B 17/320725 606/128 |
| 6,981,942 B2 | 1/2006 | Khaw | |
| 7,070,398 B2 | 7/2006 | Olsen | |
| 7,153,315 B2 * | 12/2006 | Miller | A61B 17/320725 606/159 |
| 7,229,258 B2 | 6/2007 | Wood | |
| 7,393,181 B2 | 7/2008 | McBride | |
| 7,462,019 B1 | 12/2008 | Allarie | |
| 7,927,068 B2 | 4/2011 | McBride | |
| 7,942,804 B2 | 5/2011 | Khaw | |
| 8,079,948 B2 | 12/2011 | Shifflette | |
| 8,142,501 B2 * | 3/2012 | Macossay-Torres | A61F 2/08 623/13.2 |
| 8,449,443 B2 | 5/2013 | Rodefeld | |
| 8,721,517 B2 | 5/2014 | Zeng | |
| 8,734,331 B2 | 5/2014 | Evans | |
| 8,944,748 B2 * | 2/2015 | Liebing | A61M 1/101 415/1 |
| 9,339,596 B2 * | 5/2016 | Roehn | F04D 29/247 |
| 9,416,783 B2 * | 8/2016 | Schumacher | F04D 3/00 |
| 9,416,791 B2 * | 8/2016 | Toellner | F04D 29/18 |
| 9,771,801 B2 * | 9/2017 | Schumacher | F01D 5/02 |
| 2007/0118079 A1 | 5/2007 | Moberg | |
| 2007/0233041 A1 | 10/2007 | Gellman | |
| 2008/0103591 A1 | 5/2008 | Siess | |
| 2009/0093764 A1 | 4/2009 | Pfeffer | |
| 2011/0034874 A1 | 2/2011 | Reitan | |
| 2011/0160645 A1 * | 6/2011 | Sutermeister | A61B 17/320725 604/22 |
| 2011/0257462 A1 | 10/2011 | Rodefeld | |
| 2011/0264039 A1 * | 10/2011 | Thielen | A61M 25/104 604/103.01 |
| 2012/0078232 A1 | 3/2012 | Schulting | |
| 2013/0045107 A1 | 2/2013 | Topaz | |
| 2013/0066140 A1 | 3/2013 | McBride | |
| 2014/0128659 A1 | 5/2014 | Heuring | |
| 2015/0150586 A1 * | 6/2015 | Aggerholm | A61B 17/320725 606/159 |
| 2016/0271309 A1 * | 9/2016 | Throckmorton | A61M 1/1024 |

FOREIGN PATENT DOCUMENTS

| | | |
|---|---|---|
| WO | WO 2010127871 A1 | 11/2010 |
| WO | WO 2011035926 A1 | 3/2011 |
| WO | WO 2011035929 A2 | 3/2011 |
| WO | WO 2011076439 A1 | 6/2011 |
| WO | WO 2011089022 A1 | 7/2011 |
| WO | WO 2012007141 A1 | 1/2012 |

OTHER PUBLICATIONS

Hsu, P., et al., "Review of Recent Patents on Foldable Ventricular Assist Devices", Recent Patents on Biomedical Engineering, 5, 208-222, 2012.
Kozik, D. J., et al., "Mechanical circulatory support", Organogenesis 7:1, 50-63, Jan./Feb./Mar. 2011.
Magneticbearings.org, http://www.magneticbearings.org/ventricular-assist-device/, Mar. 2015.
Sciolino, M. G., "Development, Optimization, and Twisted Adjustment of an Axial Flow Blood Pump for Fontan Patients", Thesis or Dissertation for Degree of Master of Science in Mechanical and Nuclear Engineering, Virginia Commonwealth University, Jul. 2012.
Song, X., et al., 2004, "Design and transient computational fluid dynamics study of a continuous axial flow ventricular assist device", ASAIO Journal, 215-224, 2004.
Texas Children's Hospital, Berlin Heart VAD, http://www.texaschildrens.org/Berlin-Heart/, Jan. 1-4, 2015.
Throckmorton, A. L, et al., "Numerical, Hydraulic, and Hemolytic Evaluation of an Intravascular Axial Flow Blood Pump to Mechanically Support Fontan Patients", Annals of Biomedical Engineering 39:1, 324-336, Jan. 2011.
Throckmorton, A. L, et al., "Filament Support Spindle for an Intravascular Cavopulmonary Assist Device", Artificial Organs 34:11, 1039-1044, 2010.
Throckmorton, A. L, et al., "Numerical Design and Experimental Hydraulic Testing of an Axial Flow Ventricular Assist Device for Infants and Children", ASAIO Journal, 754-761, 2007.
Throckmorton, A. L, et al., "Controlled Pitch-Adjustment of Impeller Blades for an Intravascular Blood Pump", ASAIO Journal, 382-389, 2012.
Yamazaki, K., et al., "An Intraventricular Axial Flow Blood Pump Integrated With a Bearing Purge System", ASAIO Journal 41: M327-M332, 1995.

* cited by examiner

IMPELLERS, BLOOD PUMPS, AND METHODS OF TREATING A SUBJECT

CROSS-REFERENCES TO RELATED APPLICATION

This application claims priority under 35 U.S.C. § 119(e) to U.S. Provisional Patent Application Ser. No. 62/136,382, filed Mar. 20, 2015. The entire content of this application is hereby incorporated by reference herein.

BACKGROUND OF THE INVENTION

In a normal cardiac physiology, the human heart consists of two ventricles or pumping chambers. As depicted in FIG. 1A, the left ventricular (LV) chamber drives blood through the body and end-organs via the aorta (Ao), while the right ventricle (RV) pumps blood to the lungs for gas exchange via the left pulmonary artery (LPA) and the right pulmonary artery (RPA).

Whether as a result of acquired or congenital heart disease, failure of the cardiovascular system is a progressive and debilitating disease that affects tens of millions of people worldwide. In the U.S., approximately 7 million people suffer from heart failure and hundreds of thousands of new cases are diagnosed each year. This costs the healthcare industry tens of billions annually, and only a few thousand donor hearts are available each year. Thousands are registered awaiting a donor heart, with many patients dying while on the waiting list.

In addition, thousands of infants, however, are born each year with abnormal cardiac physiology due to congenital heart defects and cardiac structural disorders. The incidence of congenital heart defects is reported to be approximately 4-10 of every 10,000 live births in the United States. Those defects having the highest complexity, such as hypoplastic left heart syndrome and tricuspid atresia, lead to a single ventricle physiology, requiring invasive heart surgery in the first year of life. These patients utilize healthcare resources disproportionate to their numbers with treatment costs exceeding $1.4 billion annually.

Patients exhibiting a single ventricle physiology typically undergo three staged palliative cardiac surgeries. Each surgery progressively offloads the single ventricle while allowing time for growth, development, and adaptation to the altered physiology. The Fontan procedure is the final surgical stage providing separation of the pulmonary and systemic circulations and creation of the total cavopulmonary connection (TCPC) where the inferior vena cava (IVC) and superior vena cava (SVC) are joined directly to feed the pulmonary arteries. In contrast to a normal cardiophysiology having two main pumping chambers (ventricles), a Fontan physiology has only one single ventricle to drive and draw blood flow through both the systemic and pulmonary circulations. In this anatomic configuration depicted in FIG. 1B, blood flows passively from the venous system into the lungs without a subpulmonary power source or right ventricle to provide the requisite pressure boost to push blood to the left atrium (LA). This total cavopulmonary connection (TCPC) is analogous to fluid flow in a four-way intersection with 2 offset inputs (SVC and IVC) and 2 primary outputs (left and right pulmonary arteries) in a cross-like orientation. After the Fontan procedure, elevated central venous pressures have been linked to mounting complications, including liver disorders, cardiac arrhythmias, and thrombosis, or clot formations. Few therapeutic alternative treatments exist, except for a heart transplant if the patients can survive the waiting period. Clinically-approved blood pumps or ventricular assist devices (VADs) are not ideal treatment options because these are designed for patients with normal anatomy and heart failure, not for patients having dysfunctional or failing Fontan physiology.

The treatment of single ventricle anomalies represents a formidable challenge for clinicians caring for patients with congenital heart disease. The incidence of children born with a single ventricle heart is about 2 per 1000 births. Over their lifespan, these patients utilize healthcare resources disproportionate to their numbers. Hospitalization costs exceed $1.4 billion per year for this cohort of patients and constitute an emerging public health concern. These patients live with a near compromised circulatory status due to their unique, anatomic cardiophysiology. As a result, individuals with a univentricular Fontan circulation are at high risk of developing complications of systemic venous hypertension, thromboembolism, and CHF. Approximately 25% of the $1^{st}$ generation of Fontan recipients will develop heart failure within 15 years, while the $2^{nd}$ generation appears to be living longer with 87% surviving to 10 years. Heart transplantation for these patients is a treatment option if they can be stabilized and survive the organ waiting period. Only modest improvements in outcomes of surgical repair have been achieved. In an effort to improve stability and survival, mechanical support strategies have been increasingly applied. Currently available ventricular assist devices (VADs), however, are designed for use in unhealthy biventricular circulations, not single ventricle configurations.

SUMMARY OF THE INVENTION

One embodiment of the invention provides a variable pitch impeller for a blood pump. The variable pitch impeller includes: a flexible polymer defining a plurality of blades extending from a first end to a second end, the blades having a resting non-zero pitch; an external shaft coupled to a first end of the flexible polymer; and an internal shaft received within the external shaft and coupled to the second end of the flexible polymer. The internal shaft and the external shaft are rotatable with respect to each other to achieve a blade pitch between about 0.0001° and about 2,880°.

This aspect of the invention can have a variety of embodiments. The plurality of blades can include between 2 and 10 blades. The plurality of blades can be arranged at substantially uniform angles about the impeller.

The variable pitch impeller can further include one or more fixed blades. The one or more fixed blades can be located at a substantially opposite end of the impeller from the plurality of blades.

The plurality of blades can have a height between about 0.1 mm and about 15 mm. The plurality of blades can have uniform heights. The plurality of blades can have variable heights.

The impeller can have an external diameter between about 3 mm and about 28 mm.

The flexible polymer can include one or more selected from the group consisting of: piezoelectric polymers and electroactive polymers. The flexible polymer can include biocompatible polyurethane. The flexible polymer can be modualarly decouplable from the external shaft and the internal shaft.

The variable pitch impeller can be fabricated entirely from non-ferrous materials. The inner shaft can be fabricated from a bronze alloy.

Another aspect of the invention provides a variable pitch impeller for a blood pump. The variable pitch impeller includes: a flexible polymer defining a plurality of blades extending from a first end to a second end; an external shaft coupled to a first end of the flexible polymer; and an internal shaft received within the external shaft and coupled to the second end of the flexible polymer. The internal shaft and the external shaft are rotatable with respect to each other to achieve a blade pitch of at least 2.8°/mm.

This aspect of the invention can have a variety of embodiments. The internal shaft and the external shaft can be rotatable with respect to each other to achieve a blade pitch of at least 8.0°/mm. The internal shaft and the external shaft can be rotatable with respect to each other to achieve a blade pitch of at least 11.0°/mm.

Another aspect of the invention provides an impeller for a blood pump. The impeller includes: a plurality of helical blades extending from a first end to a second end. The helical blades have a blade pitch of at least 2.8°/mm.

This aspect of the invention can have a variety of embodiments. The helical blades can have a blade pitch of at least 8.0°/mm. The helical blades can have a blade pitch of at least 11.0°/mm.

Another aspect of the invention provides a blood pump including the variable pitch impeller as described herein.

This aspect of the invention can have a variety of embodiments. The blood pump can have an expanded diameter of 28 mm or less. The impeller can be supported within the blood pump by one or more bearings. The one or more bearings can be magnetic bearings.

Another aspect of the invention provides a method of treating a subject having a cardiac condition. The method includes: introducing a variable pitch impeller as described herein into a cardiac passage; and rotating the variable pitch impeller to improve blood flow within the subject.

This aspect of the invention can have a variety of embodiments. The cardiac structure can be selected from the group consisting of: a ventricle, a left ventricle, and a right ventricle. The variable pitch impeller can be introduced percutaneously.

Another aspect of the invention provides an impeller including: a non-ferrous frame, a polymer defining a plurality of blades over the frame; and a non-ferrous shaft coupled to the non-ferrous frame.

This aspect of the invention can have a variety of embodiments. The non-ferrous shaft can be a bronze flexible cable. The non-ferrous shaft can be surrounded by a polymeric sheath. The polymeric sheath can be coupled to a trailing end of the non-ferrous frame. The non-ferrous shaft can be coupled to a leading end of the non-ferrous frame.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 6A depicts a physical 400° prototype impeller. FIG. 6B depicts an experimental testing system including an impeller prototype (a), an inlet tank (b), an outlet tank (c), a pressure transducer (d), a resistance clamp (e), an ultrasonic flow probe (f), an ultrasonic flow meter (g), a pressure transducer signal conditioner (h), an oscilloscope (i), a motor (j), a motor power supply and controller (k), and data acquisition device (1). FIG. 6C depicts a schematic diagram of another embodiment of an experimental testing system according to an embodiment of the invention.

DEFINITIONS

Figure 1B:
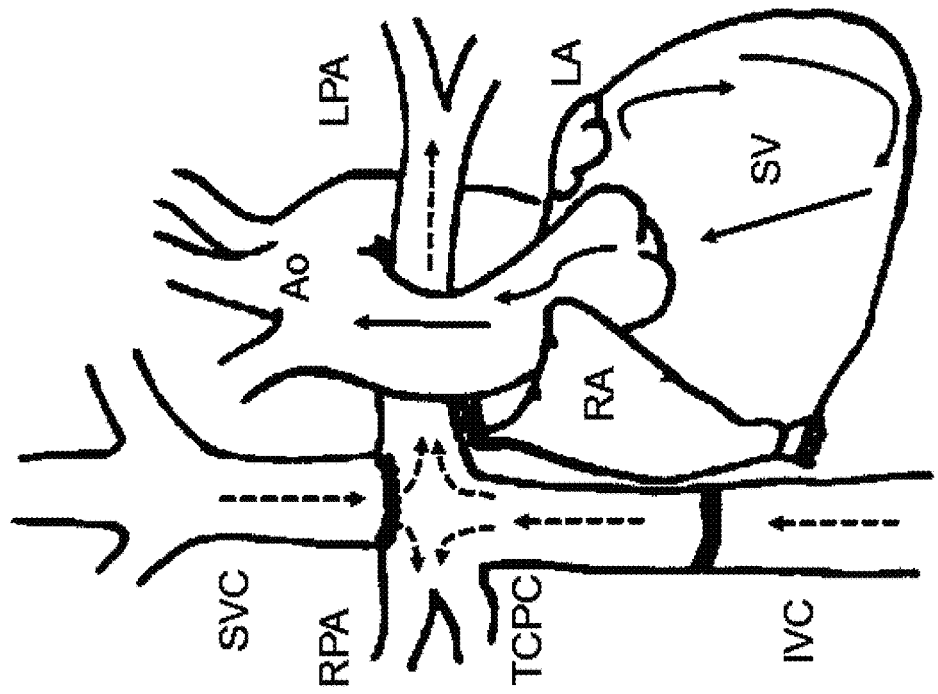
FIG. 1B depicts single ventricle physiology, in which the right side of the heart is bypassed with deoxygenated blood flowing from the body into the pulmonary arteries. The single ventricle becomes the left ventricle and pumps oxygenated blood to the body. In both figures, the flow of deoxygenated blood is depicted in dashed lines and the flow of oxygenated blood is depicted in solid lines. Anatomical features are abbreviation as follows: Ao—aorta; RA—right atrium; LA—left atrium; RV—right ventricle; LV—left ventricle; SV—single ventricle; PV—pulmonary vein; RPA—right pulmonary artery; LPA—left pulmonary artery; SVC—superior vena cava; IVC—inferior vena cava; and TCPC—total cavopulmonary connection.
Figure 1A:
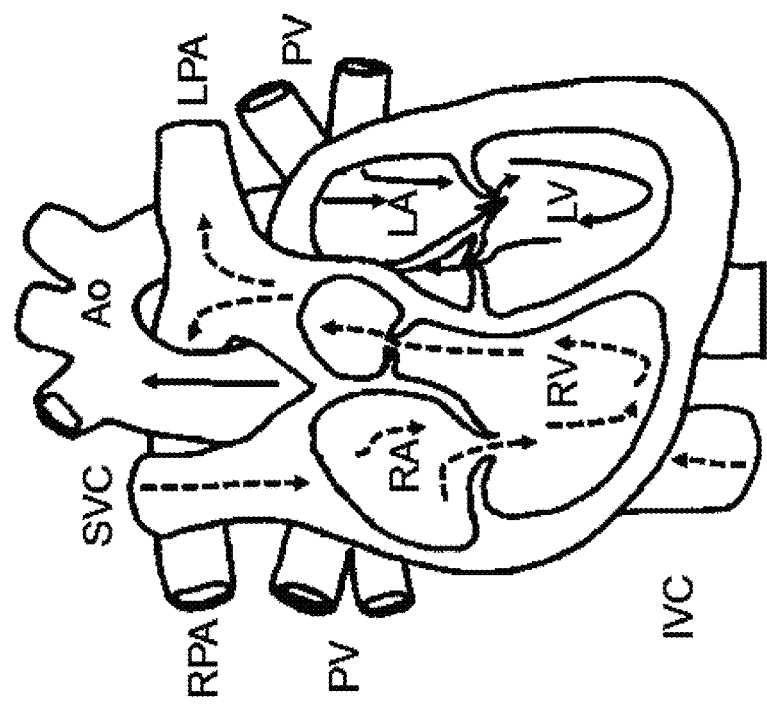
FIG. 1A depicts a normal heart physiology.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Aspects of the invention provide impellers and mechanical circulatory support (MCS) devices that can significantly advance the therapeutic treatment of thousands of cardiac patients each year. Aspects of the invention address avoid or minimize complications (e.g., thrombosis and blood cell trauma) associated with conventional blood pumps and ventricular assist devices, e.g., by incorporating active/dynamic control of blood flow to mitigate irregular flow patterns and reduce the propensity of clotting and hemolysis. Aspects of the invention uniquely combine minimally-invasive endovascular therapy with mechanical circulatory support (MCS) technology having flow control capabilities. Aspects of the invention provide axial flow blood pump geometries capable of percutaneous insertion and blade pitch-adjustment for placement in strategic locations in the systemic or pulmonary circulation for patients having dysfunctional single ventricle physiology or biventricular physiology in acute or chronic clinical settings.

Aspects of the invention provide a new MCS device to support patients with impaired cardiovascular function. This device could be employed in the systemic circulation or pulmonary circulation depending upon the impeller geometry. In one embodiment, the MCS device is a ventricular assist device (VAD) having a pitch-adjustable impeller. The integration of controlled pitch-adjustment into VADs will enhance blood flow conditions, improve pressure generation, and reduce irregular flow patterns that are produced during on- and off-design pump operation. In particular, embodiments of the invention will facilitate flow control and higher energy transfer for intravascular blood pumps of the pulmonary circulation or systemic circulation system.

As a new treatment strategy for Fontan patients, embodiments of the invention provide a collapsible, percutaneously-inserted, axial flow blood pump to support the cavopulmonary circulation of adolescent and adult Fontan patients with dysfunctional single ventricle physiology. The embodiments described herein are the result of careful consideration of biophysical factors, such as hemolysis, biocompatibility, implantability, device control, pump performance, biomaterials, and thrombosis. Embodiments of the invention produce flow rates of 0.5-4 L/min with pressure rises of 2-25 mmHg for 1,000-9,000 RPM. The flow and pressure range falls within expected levels to mechanically support Fontan patients.

Figure 2A:
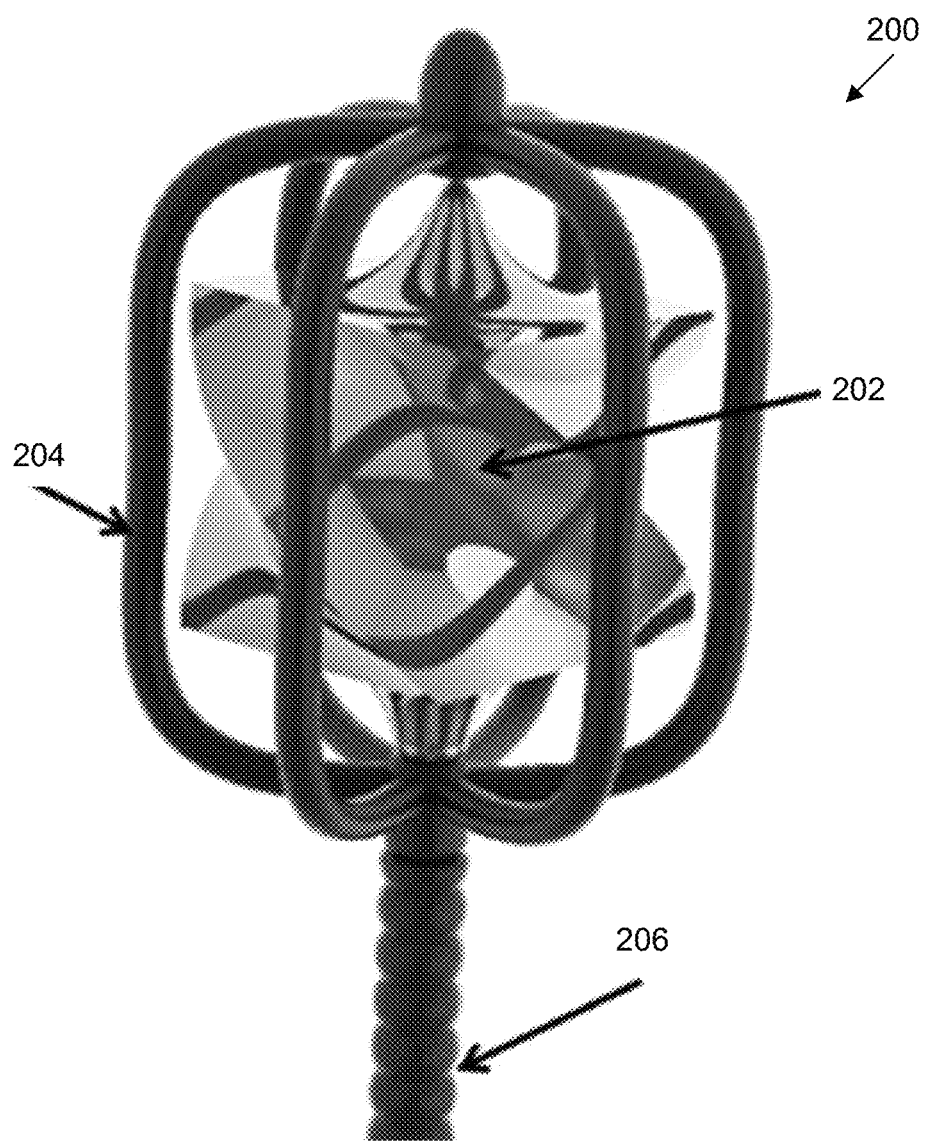
FIG. 2A depicts an axial flow blood pump according to an embodiment of the invention. The design includes a catheter, protective cage of filaments, impeller blade set, and outlet nose cap.
Figure 2B:
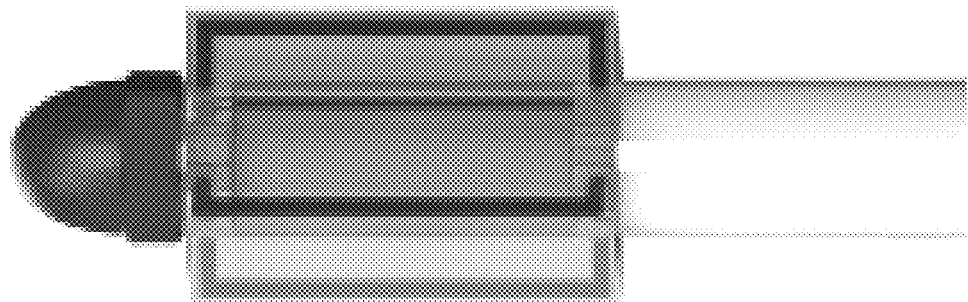
FIGS. 2B and 2C depicts an axial flow blood pump in untwisted and twisted configurations, respectively, according to another embodiment of the invention.
Figure 2C:
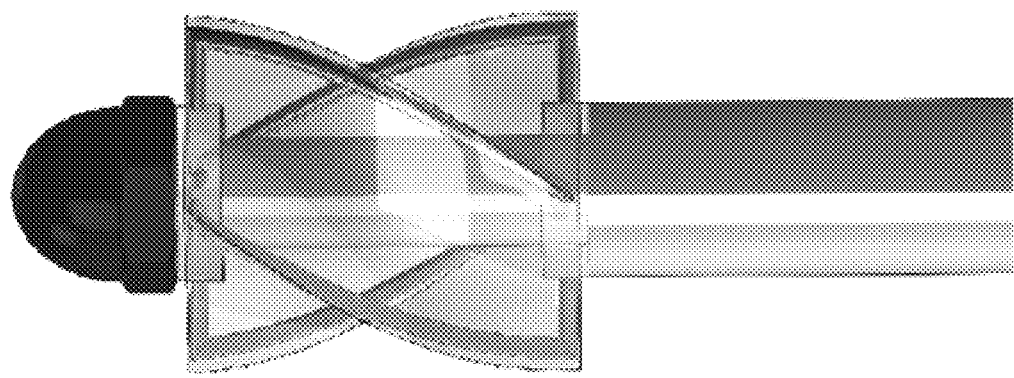
Figure 2D:
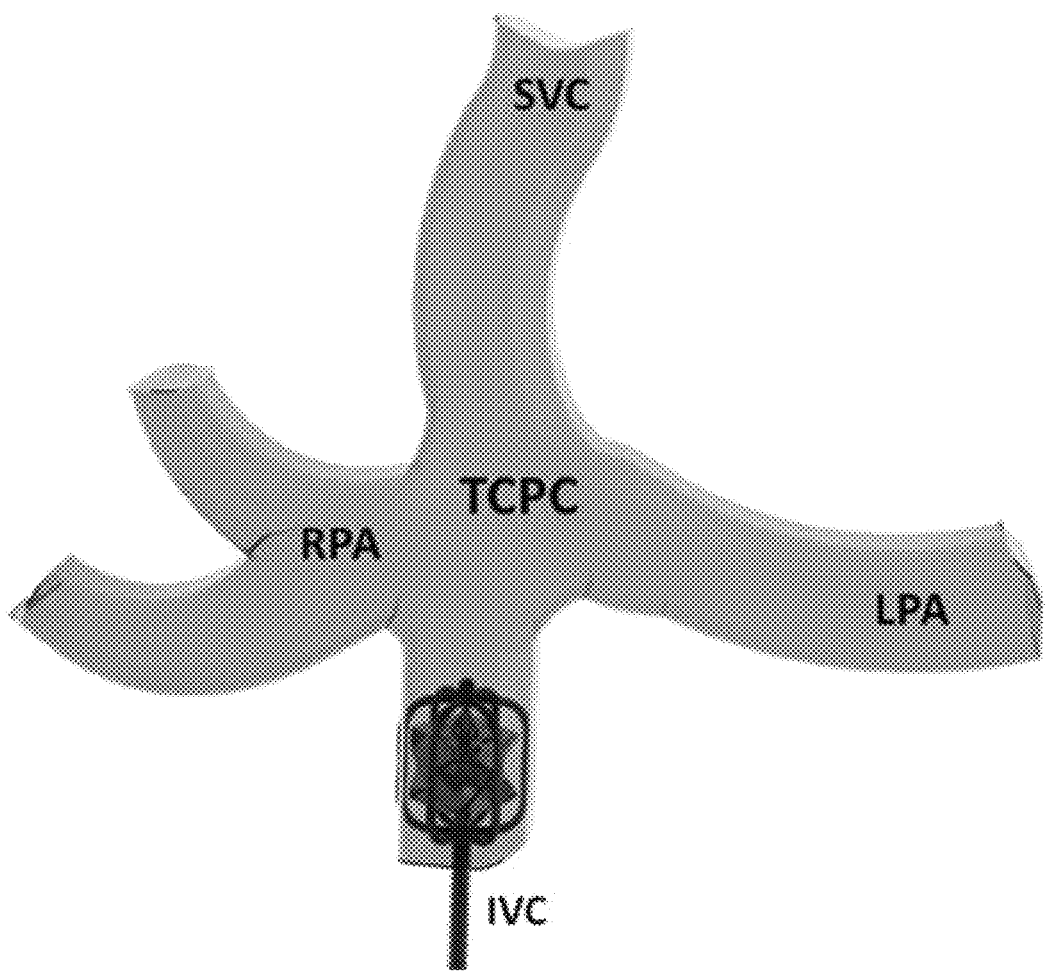
FIG. 2D depicts the percutaneous placement of the blood pump in the inferior venous cava (IFC) according to an embodiment of the invention. The intravascular pump can be placed in other veins or arteries in order to address various clinical needs.

FIG. 2A illustrates the conceptual design of an embodiment of this new medical device. The pump 200 includes three main components: a rotating impeller 202 that imparts energy to the fluid, a stationary protective cage or stent 204 that has radially arranged filaments as touchdown surfaces to protect the vessel wall from the rotating impeller blades, and a support catheter 206 with a specially-designed flexible drive cable-fluid seal combination. An infused dextrose solution lubricates the flexible drive cable and serves as a purge fluid to flush the drive seal of accumulated blood cells.

Impeller Geometries

As described further herein, impellers can have one or more blades that can be fixed, actively movable, and/or passively moveable. Exemplary numbers of blades include 1, 2, 3, 4, 5, 6, 7, 8, 9, 10, and the like. In some embodiments, fixed blades are paired with movable blades. For example, one end of the impeller can include 1-10 fixed blades while the other end of the impeller can includes 1-10 movable blades.

Blades can have a variety of heights relative to the hub of the impeller. Exemplary heights include between about 0.01 mm and about 15 mm. Blades can have the same or different heights within a blade and/or between blades.

The impeller can have an external diameter (including blade heights) between about 3 mm and about 28 mm.

The geometry of an impeller includes the hub diameter, blade root, blade tip, leading and trailing edge angles, blade thickness, pitch, skew, number of blades, and blade area (mean-width ratio). The leading and trailing edge angles of the blades are selected to achieve a particular hydraulic performance and range of operating conditions. These angles define the hydraulic performance capabilities of the impeller. Blade thickness and tip clearance between the blade and the housing for blood pumps, given the millimeter scale, is limited in part by manufacturing tolerances and the outer cage geometry. Energy transfer across an axial blood pump occurs as the blade imparts rotational energy to the fluid. Newton's law of motion, as applied to an impeller in the form of fluid traversing the rotor, states that the torque on the impeller is equal to the changing rate of angular momentum of fluid.

In contrast to ventricular assist of the systemic circulation, mechanical cavopulmonary assist requires a much lower pressure augmentation; a pressure adjustment of only 1-5 mmHg is likely sufficient to improve the hemodynamics of a Fontan patient. A moderate degree of recirculation is also desirable to facilitate surface washing of impeller blades and cage filaments. The non-obstructive flow path using the vessel wall as the pump housing is expected to assist in the maintenance of a continuous surface washing effect and minimize regions of recirculation or stagnant flow that might encourage protein or platelet deposition. Optimization of the impeller geometry was performed through parametric analysis of the blade pitch in which computational simulations provided valuable data about the impact on the hydraulic performance.

Applicant utilized three-dimensional computer aided design (CAD) software (SolidWorks 2014, Dassault Systems, Concord, Mass.) to develop the impeller designs described herein. Applicant developed 6 axial-flow impeller geometries from first principles and modified the angle of twist or pitch of the impeller blades from 100° to 600° at 100° intervals. Applicant also refined the design with focused iterations between 300° and 400° of blade twist at 20° increments.

Figure 3:
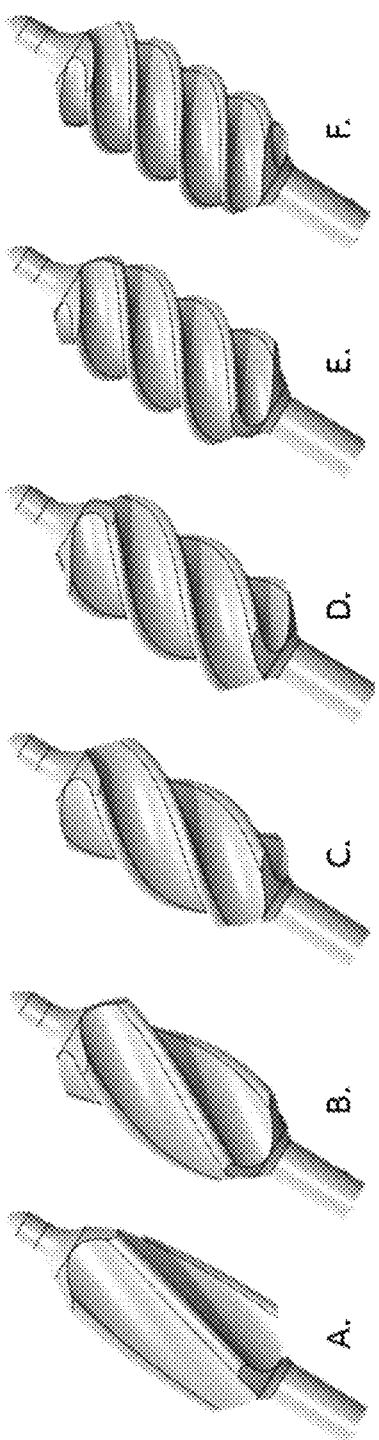
FIG. 3 depicts cavopulmonary impeller designs having between 100° and 600° of blade twist in 100° increments according to embodiments of the invention. Panels A, B, C, D, E, and F depict impellers with 100°, 200°, 300°, 400°, 500°, and 600°, respectively.
Figure 4:
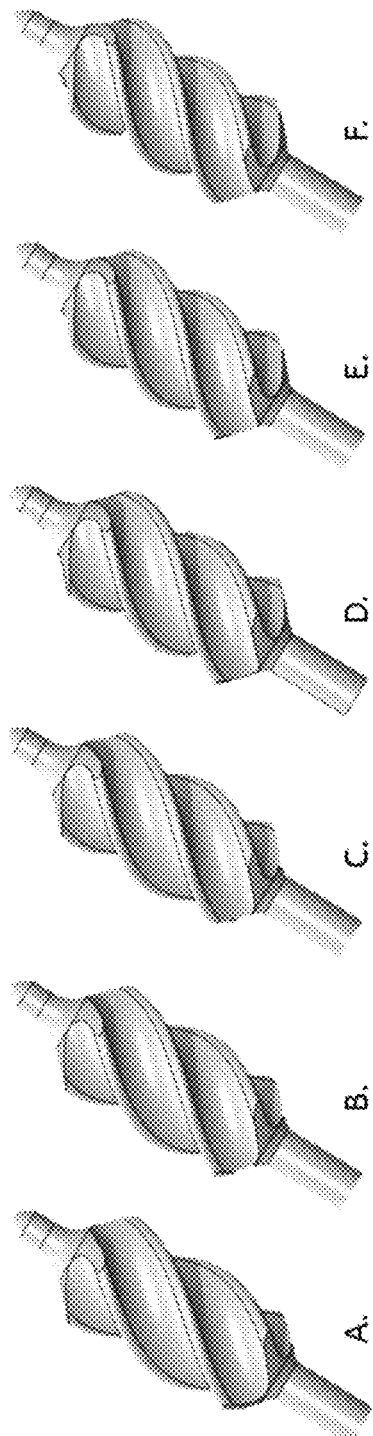
FIG. 4 depicts cavopulmonary impeller designs having between 300° and 400° of blade twist in 20° increments according to embodiments of the invention. Panels A, B, C, D, E, and F depict impellers with 300°, 320°, 340°, 360°, 380°, and 400°, respectively.

FIG. 3 displays various impeller geometries according to embodiments of the invention.

Figure 5:
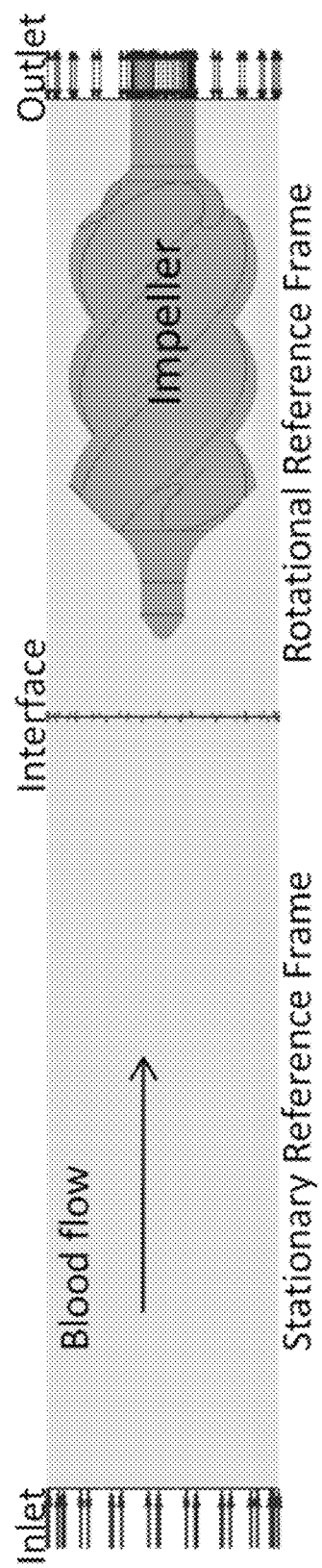
FIG. 5 depicts a computational model of the inlet region and twisted impeller design according to an embodiment of the invention.

An inlet pipe was placed at the inflow of the impeller models in order to support fully developed flow profiles entering the bladed region. As an example, FIG. 5 illustrates the computational model for the 300° twisted configuration.

Computational Analyses

A commercial computational flow dynamics (CFD) software package (ANSYS 15.0, ANSYS, Inc., Canonsburg, Pa.) was utilized to simulate flow across the impellers. A tetrahedral element mesh of the impeller domains was constructed having approximately 3.3 million elements and the placement of inflation layers at the surfaces to satisfy the constraints of the turbulence model. A grid density and convergence study were performed. The mesh was systematically refined through incremental adjustments until grid independence was achieved. The solver convergence criteria was set to establish convergence when a residual error of less than $1 \times 10^{-3}$ was achieved. Turbulent flow conditions are expected to dominate in the impeller domain with Reynolds numbers (Re) above 4000. The k-ε turbulence model described in A. L. Throckmorton et al., "Numerical, hydraulic, and hemolytic evaluation of an intravascular axial flow blood pump to mechanically support Fontan patients," 39(1) *Ann. Biomed. Eng.* 324-336 (2011) was employed. The computational models, including inlet pipe and impeller domain, were imported into the ANSYS-CFX solver to execute the simulations as in J. Y. Kapadia et al., "Hydraulic testing of intravascular axial flow blood pump designs with a protective cage of filaments for mechanical cavopulmonary assist," 56(1) J. ASAIO 17-23 (2010); Throckmorton 2011; and S. S. Bhaysar, "Intravascular mechanical cavopulmonary assistance for patients with failing Fontan physiology," 33(11) *Artif. Organs* 977-87 (2009).

Boundary Conditions

Flow through the pump domain was set to be steady flow, and a no-slip boundary condition was applied to the stationary walls of the model. In the stationary reference frame, the inlet and outlet of the impeller were defined as stationary boundaries. The impeller was specified to be in the rotating reference frame with rotation in the counterclockwise direction as required by the impeller blade orientation. The frozen rotor interface connected regions of differing reference frames (i.e., inlet pipe and impeller domain) and maintained flow properties. The frozen rotor interface enables the vessel wall to appear rotating while adding a source momentum term to the nodal calculations thereby simulating rotation. Implementation of the frozen rotor approach means that the mesh is itself not rotating as would be found in a transient rotor-stator analysis. A fluid viscosity value of 0.0035 kg/m*s and a fluid density of 1,050 kg/m³ were used for the fluid properties in the simulations. A uniform mass inflow rate was specified for each simulation. The pump rotational speeds were evaluated at 6,000-10,000 RPM for twisted blade positions of 100°-600° and the refined range of 300°-400° at 20° increments. The outlet boundary condition was defined to have a physiologic pressure. The outlet boundary surface was specified as an opening in order to capture irregular flow patterns, if present in the outflow region.

Quasi-Steady Simulations

As an extension of the steady-flow analyses, a quasi-steady study was performed on the 300° twisted pump geometry. The purpose of this study was to more closely determine the ideal blade twist angle and to assess if blade orientation led to unusual pressure losses. The impeller mesh domain was manually and incrementally rotated by 6° using the frozen-rotor interface; this produced an entirely separate simulation for each 6° of rotation. A total of 60 additional simulations were executed. The new domain position at each rotational increment was of the same mesh quality with similar attributes (i.e., number of nodes and elements) as compared to the original mesh. The boundary conditions for these simulations were specified according to the previously prescribed set in the steady flow simulations.

Blood Damage Predictions

In consideration of biophysical factors, a blood damage analysis was conducted using CFD to assess the potential damage to red blood cells resulting in thrombosis or hemolysis. The blood damage model calculated a damage index, which is a weighted level of scalar stress and exposure time to such levels of stress. The three-dimensional stress field was determined, including the six terms of the scalar stress tensor (i.e., normal and shear components), according to Equation 1 below.

$$\sigma = \left(\frac{1}{6}\sum [\sigma_{ii} - \sigma_{jj}]^2 + \sum \sigma_{ij}^2\right)^{\frac{1}{2}} \quad (1)$$

Applicant sought a pump design having shear stress levels below 425 Pa and exposure times that are shorter than 600 ms. The fluid streamlines generated by the impeller were also examined to numerically predict fluid residence times in the pump domain. A power law relationship was employed in this blood damage analysis to relate residence time and the scalar stresses in the estimation of a blood damage index, according to Equation 2 below.

$$D = \sum_{inlet}^{outlet} 1.8 \times 10^{-6} \times \sigma^{1.991} \times \Delta t^{0.765} \quad (2)$$

By computationally stepping along the flow streamlines, the accumulated shear stress and residence times were tracked and summed to estimate the potential for blood damage by the impeller.

In Equation (2), D represents the blood damage index and indicates a percentage of damaged red blood cells, t is the stress exposure time, σ is the fluid shear stress from Equation (1), and the summation symbol indicates the addition of the accumulated time and stress between the inlet and outlet faces of the CFD model. A blood damage index of below 2% is the target design. A total of approximately 730 particles were released at the model inlet and were tracked through the model to the outlet. Data processing and analysis occurred using a custom written MATLAB® code (MATLAB 2014, The Mathworks, Natick, Mass.) that computed the blood damage according to Equation (2). The blood damage estimations were performed for a flow rate of 3.0 L/min at 7000 RPM.

Experimental Testing of Impeller Prototype

Figure 6B:
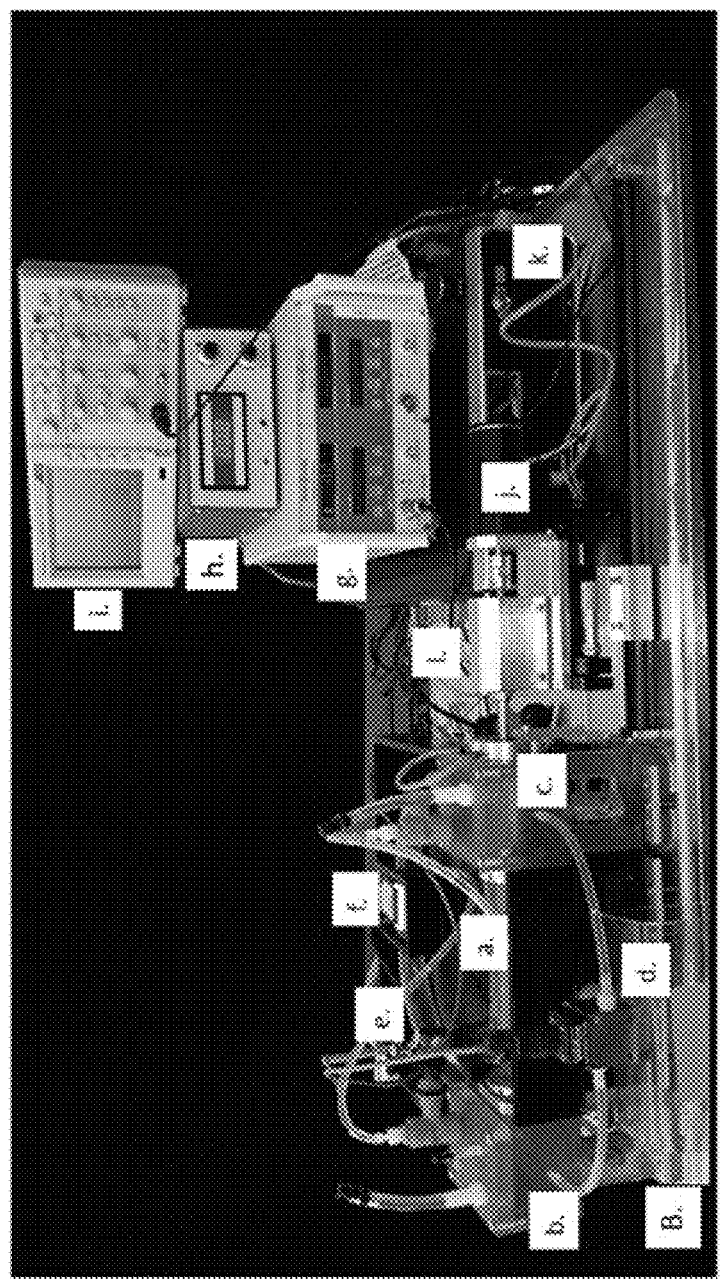
FIGS. 6A-6C depict hydraulic testing of impellers according to an embodiment of the invention.
Figure 6A:
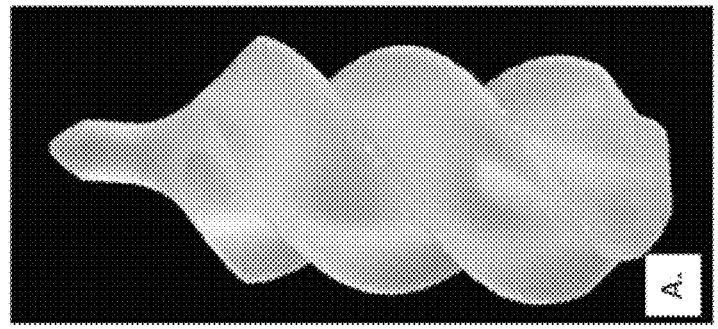
Figure 6C:
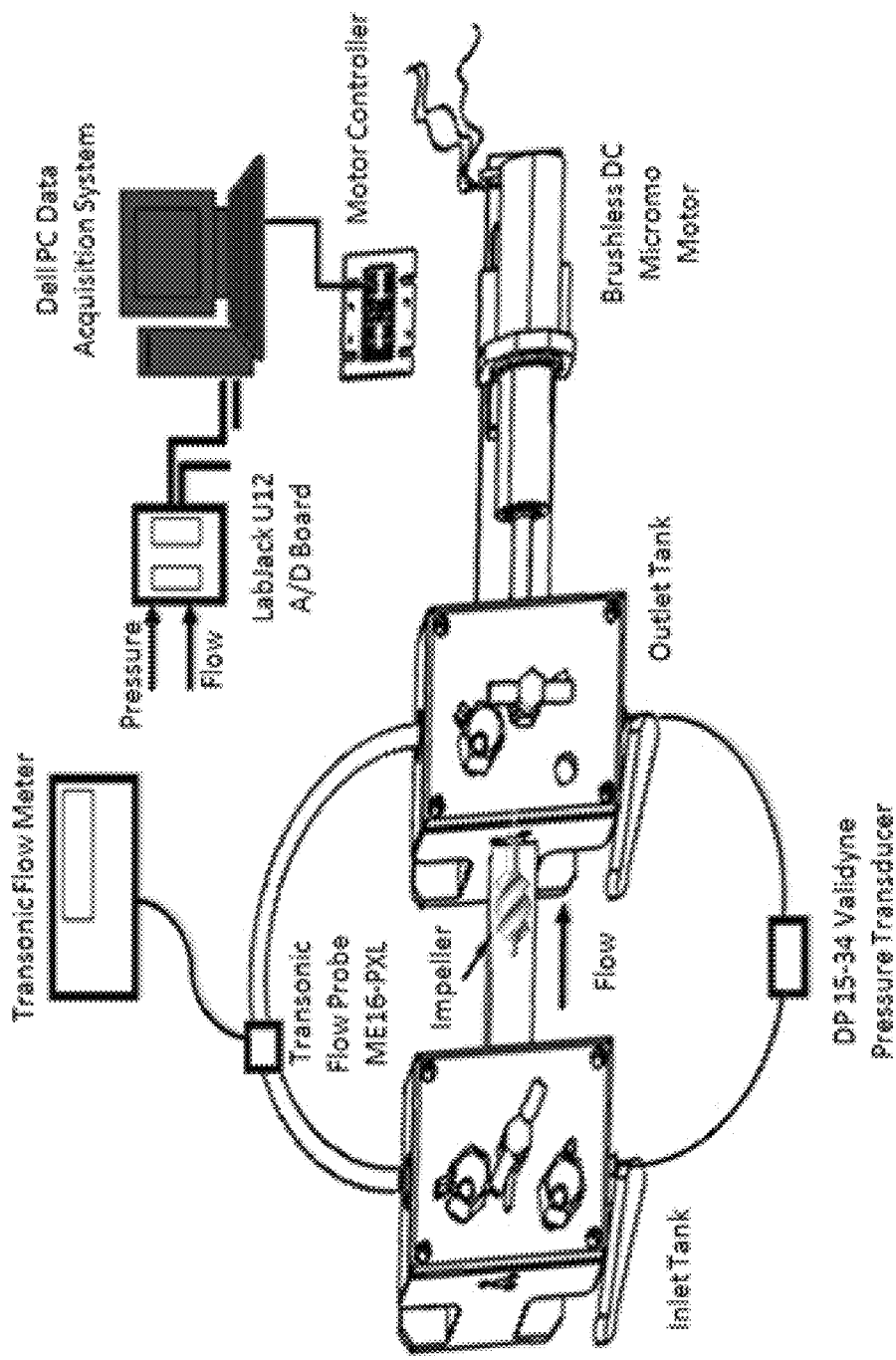

The twisted impeller geometry with the highest pressure generation (i.e., a blade twist angle of 400°) was selected for manufacturing by rapid prototyping. An industrial partner (ART, Inc., Fredericksburg, Va.) performed the stereolithography (SLA). The physical prototype (depicted in FIG. 6A) was manufactured from a WATERSHED® resin available from Koninklijke DSM N.V. of Elgin, Ill. An existing experimental setup for evaluating prototype impellers shown in FIG. 6B was utilized for the hydraulic experiments.

The prototype impeller included four helically wrapped blades at a specific blade twist angle of 400°. The prototype was 36 mm in length with a hub diameter of 14 mm. The blade height on the trailing edge was 4 mm. The testing system included an inlet reservoir of fluid for the impeller to draw from and an outlet reservoir to receive the transported fluid volume. An acrylic tube with an internal diameter of 18 mm was used to model the vessel wall or pump housing. The blade tip clearance between the impeller and the wall was 2 mm.

Additional components of the test rig included a section of TYGON® tubing to connect the two reservoirs and return fluid volume to the inlet reservoir. An ultrasonic flow meter and flow probe provided measurements of the flow generated by the impeller. A differential pressure transducer and signal conditioner (DP15-34, Validyne Engineering, Inc., Northridge, Calif.) was used to measure the pressure rise across the pump impeller. An adjustable clamp enabled the control of the flow rate on the TYGON® tubing. The impeller was connected to a short shaft or flexible drive cable supported by mechanical ball bearings. A brushless DC motor (MICROMO Electronics, Inc., Clearwater, Fla.) was employed to drive rotation of the shaft/cable via a shaft connecting coupling. The flow rate and pressure rise were measured using a LABJACK® U12 data acquisition board (LabJack Corporation, Lakewood, Colo.). Data was collected using a sample rate of 100 Hz.

A water/glycerin solution composed of 60% water and 40% glycerin (solution by mass) served as the working fluid and blood analog solution. A Cannon-Fenske routine viscometer (Size 50, Cannon Instrument Co., State College, Pa.) and a hydrometer (Cole-Parmer Instrument Company, Vernon Hills, Ill.) were used to verify these properties.

Quantitative Design Comparison

To effectively compare the performance of one impeller design to another, Applicant completed a non-dimensional regression analysis of the CFD data predictions as described in A. L. Throckmorton et al., "Numerical design and experimental hydraulic testing of an axial flow ventricular assist device for infants and children," 53(6) *J. ASAIO* 754-61 (2007). The discrete data points for pressure and flow are condensed into two non-dimensional coefficients for each impeller. The coefficients are represented as:

$$\Psi = C_\Psi\left(\frac{\Delta P}{\rho N^2 R^2}\right) \quad (3)$$

$$\Phi = C_\Phi\left(\frac{Q}{NR^3}\right) \quad (4)$$

where in Equation (3), $\Psi$ represents the pressure coefficient, $C_\Psi$ is a constant of $1.2157 \times 10^{10}$, $\Delta P$ is the pressure rise across the pump in mmHg, $\rho$ is the fluid density in kg/m³, N is the rotational speed of the impeller in RPM, and R represents the radius of the impeller hub in mm. For Equation (4), $\Phi$ represents the flow coefficient where $C_\Phi$ is a constant representing the flow factor equal to $1.5195 \times 10^5$ and Q signifies the flow rate in L/min. A regression analysis is then performed on both data sets by fitting a polynomial trend line. Three empirical coefficients ($\beta_0$, $\beta_1$, $\beta_2$) are generated from the regression analysis. These coefficients were used in Equation (5), where the subscript type represents a particular impeller prototype.

$$\Psi_{type} = \beta_2(\Phi_{type}^2) + \beta_1(\Phi_{type}) + \beta_0 \quad (5)$$

A Student-t and F test was performed in order to determine the statistical significance of the coefficients and the polynomial models. Applicant conducted this statistical analysis for the impeller designs and obtained separate mathematical fitted equations using SPSS® software (SPSS version 22.0, IBM Corporation, Armonk, N.Y.). The derived coefficients are listed in Table 1, along with the statistical findings.

TABLE 1

Polynomial Regression Analysis of Numerical Predictions for the Prototype Impellers

| Type | $\beta_2$ | p | $\beta_1$ | p | $\beta_0$ | P | F-test | $R^2$ | $R^2_{adj}$ |
|---|---|---|---|---|---|---|---|---|---|
| CFD 200° | 4.41 | <.0001 | −0.462 | <.0001 | 0.016 | <.0001 | <.0001 | 0.998 | 0.998 |
| CFD 300° | 4.394 | <.0001 | −0.493 | <.0001 | 0.021 | <.0001 | <.0001 | 0.998 | 0.998 |
| CFD 400° | 5.972 | <.0001 | −0.594 | <.0001 | 0.025 | <.0001 | <.0001 | 0.998 | 0.998 |
| CFD 300° | 5.048 | <.0001 | −0.49 | <.0001 | 0.016 | <.0001 | <.0001 | 0.999 | 0.999 |
| CFD 320° | 5.187 | <.0001 | −0.525 | <.0001 | 0.022 | <.0001 | <.0001 | 0.999 | 0.999 |
| CFD 340° | 5.271 | <.0001 | −0.541 | <.0001 | 0.023 | <.0001 | <.0001 | 0.999 | 0.999 |
| CFD 360° | 5.18 | <.0001 | −0.533 | <.0001 | 0.023 | <.0001 | <.0001 | 1 | 1 |
| CFD 380° | 4.987 | <.0001 | −0.538 | <.0001 | 0.024 | <.0001 | <.0001 | 1 | 1 |
| CFD 400° | 5.859 | <.0001 | −0.585 | <.0001 | 0.025 | <.0001 | <.0001 | 0.999 | 0.998 |
| Exp 400° | — | — | −0.464 | <.0001 | 0.028 | <.0001 | <.0001 | 0.993 | 0.993 |

Computational Findings

Pressure Generation

Figure 7:
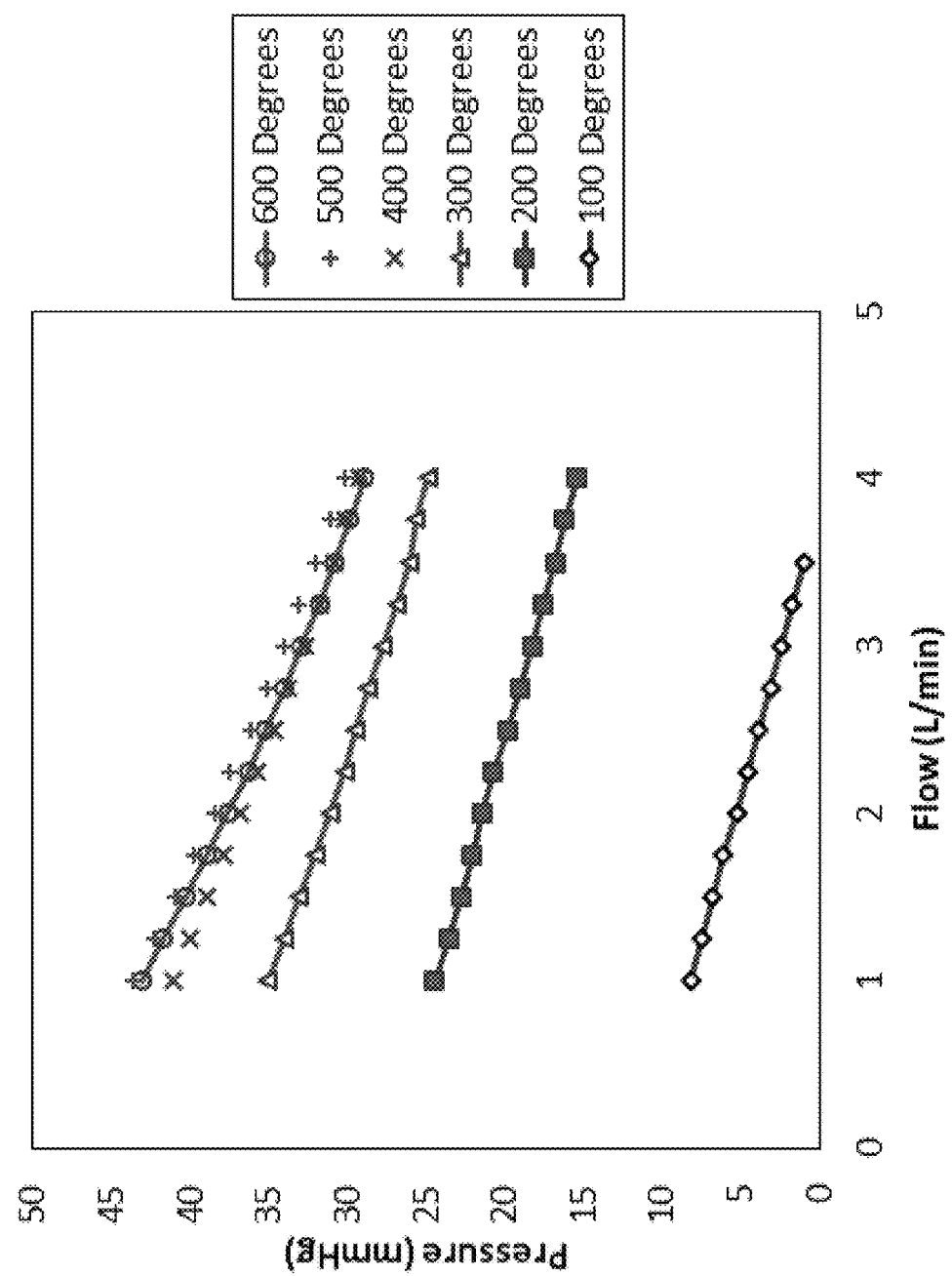
FIG. 7 depicts a comparison of pump performance for several impeller designs according to embodiments of the invention. The impellers were evaluated at a rotational speed of 10,000 RPM over a range of flow rates from 1-4 L/min.

This study evaluated the pressure rise across 6 prototype impellers with varying angles of blade twist for rotational speeds of 6,000-10,000 RPM for flow rates of 1-4 L/min. FIG. 7 shows a performance comparison of these impellers at a rotational speed of 10,000 RPM. Each data point reflects the steady state results for one CFD simulation at the predefined boundary conditions. Expected trends were found with a decrease in pressure rise as a function of increasing flow rate for a given rotational speed. It was determined that the impeller with a 100° twist performed at the lowest level, having pressures below 10 mmHg at 10,000 RPM. The impeller with twist degrees above 100° generated pressure rises above 15 mmHg. As shown in FIG. 7, the 400°, 500°, and 600° twisted impellers had pressure-flow performance curves that were clustered together with little measurable difference among the designs. The impeller with the 400° twist generated pressures above 32 mmHg for the entire flow range.

Figure 8:
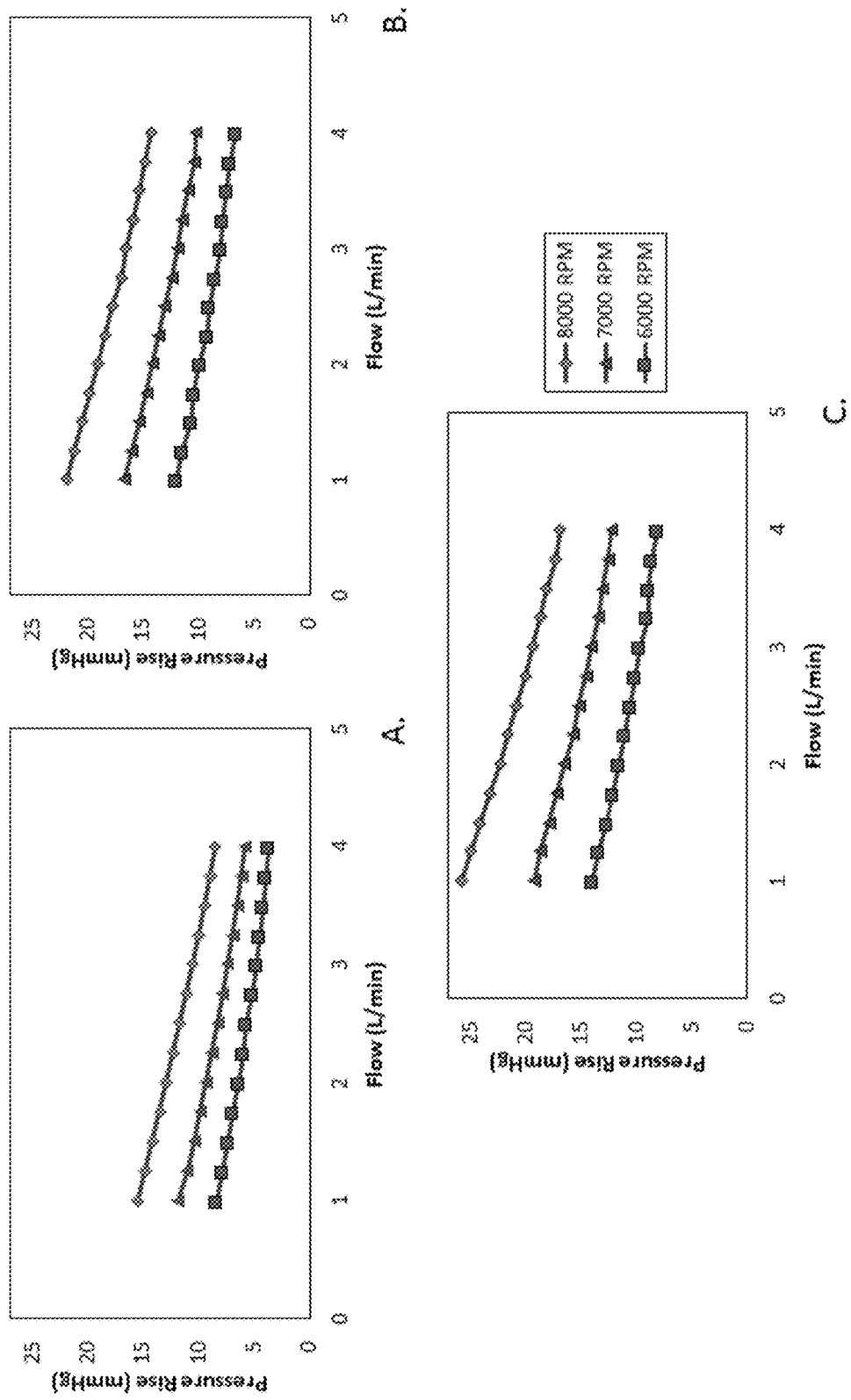
FIG. 8 depicts pump performance curves according to embodiments of the invention. The impeller designs having twists of 200° (Panel A), 300° (Panel B), and 400° (Panel C) were evaluated for a range of rotational speeds of 6,000-8,000 RPM.

FIG. 8 illustrates the pressure-flow performance of the 200°, 300°, and 400° twisted impellers for rotational speeds of 6000, 7000, and 8000 RPM. Expected trends were found with higher pressures at faster rotational speeds. The 200°, 300°, and 400° impellers generated maximum pressure rises of 16, 22, and 26 mmHg, respectively, over flow rates of 1-4 L/min.

Figure 9:
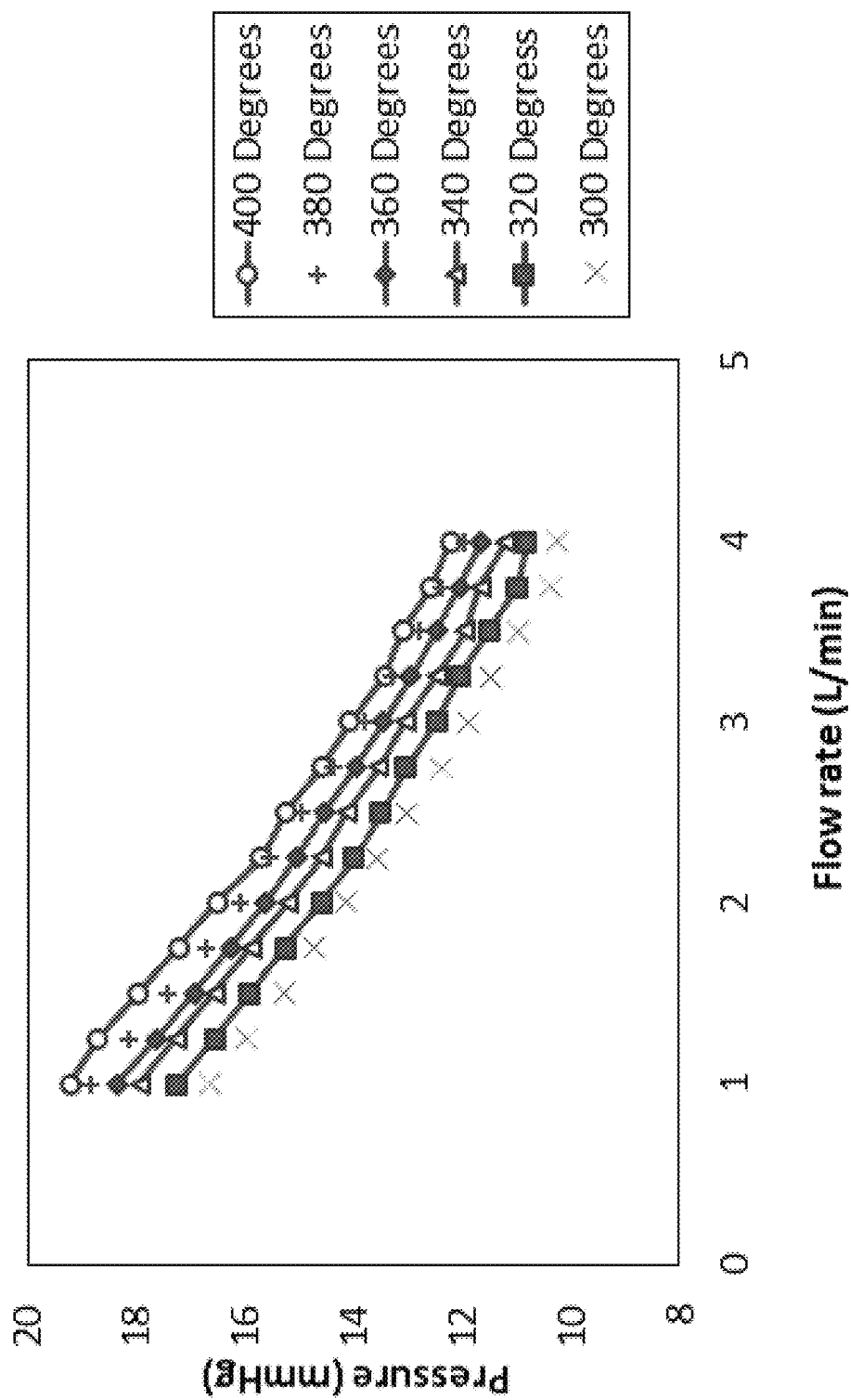
FIG. 9 depicts a comparison of pump performance curves for a refined range of impeller designs according to embodiments of the invention. The impellers in the range of 300°-400° with 20° increments of blade twist were examined for a rotational speed of 7,000 RPM.

Based on the previous simulations, Applicant refined the range of blade twist angles to between 300° and 400° degrees at 20° increments (i.e., 300°, 320°, 340°, 360°, 380°, and 400° twist). FIG. 9 demonstrates a comparison of the simulations of the pressure-flow performance for these twist angles at 7,000 RPM. It was observed that a higher twist angle produces a larger pressure generation over the entire flow range. A gain of approximately 7 mmHg of pressure rise was realized by increasing the twist angle from 300° to 400°. The 400° case produced a maximum pressure rise of 19.2 mmHg while the 300° case produced a maximum pressure rise of 16.6 mmHg at 7,000 RPM. The refined range of blade twist angles proved that the 400° impeller was the superior impeller geometry. The 400° impeller was found to have the maximum pressure generation overall generating 4-26 mmHg over flow rates of 1-4 L/min for rotational speeds of 6,000-8,000 RPM.

Quasi-Steady Study

Figure 10:
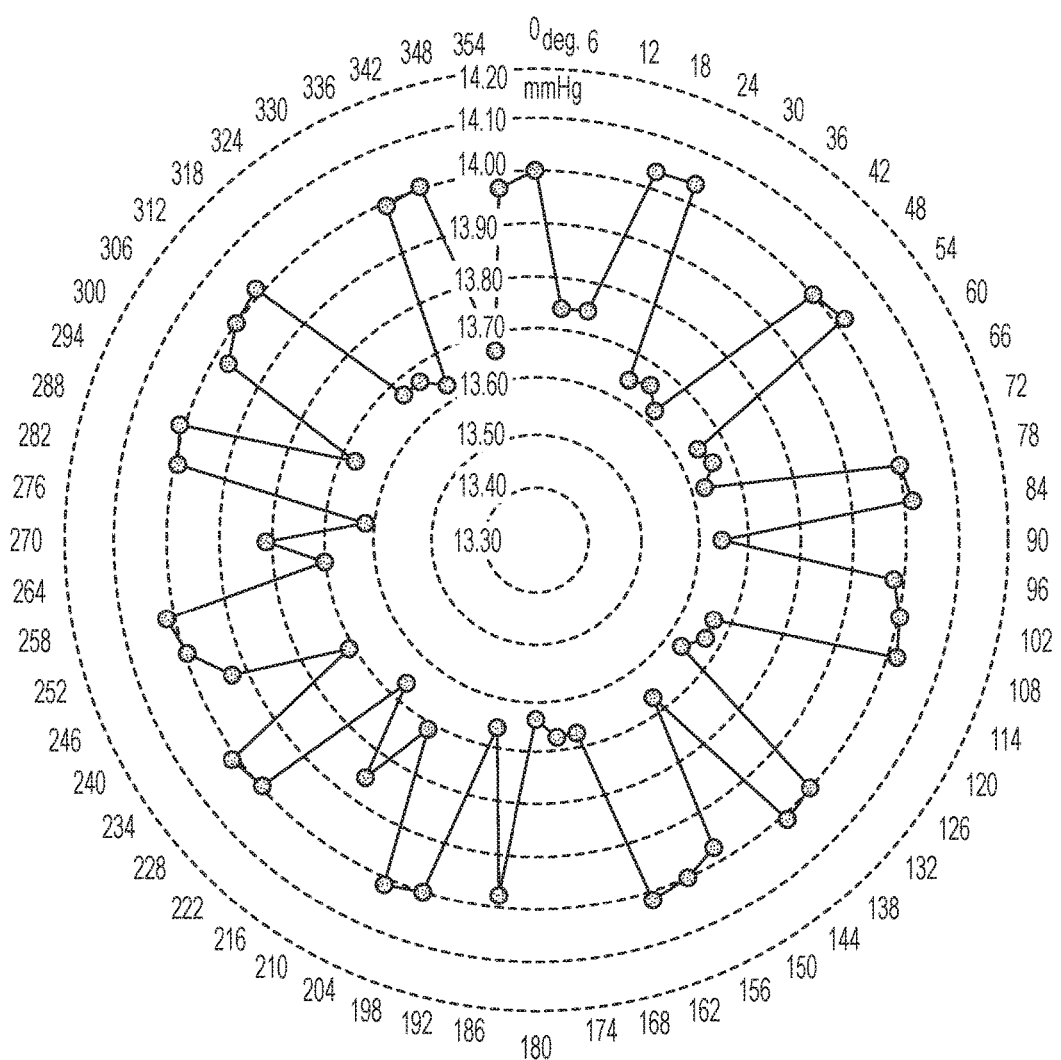
FIG. 10 depicts quasi-steady study results for a 400° twisted impeller according to an embodiment of the invention with an operating condition of 3 L/min at 7,000 RPM. The impeller was rotated at 6° increments and angular rotation of 18° and 24° had the largest pressure generation with the lowest pressure generation occurring at 42°.

A set of simulations was completed using a quasi-steady analysis to determine the impact of pressure generation as related to rotational angle for the 400° impeller design. The impeller was rotated at 6° increments requiring 60 simulations to describe the pressure waveform. The results of the quasi-steady study are shown in FIG. 10 for 3 L/min at 7,000 RPM. Given the varying position of the impeller, the pressure rise remained reasonable, between 13.75 and 14.15 mmHg. A large variation in pressure rise was not found during this quasi-steady analysis.

Quantitative Performance Comparison of Impeller Designs

A regression analysis was carried out on selected impeller designs for 200°, 300°, and 400° of blade twist to compare the pump performance. A separate and secondary analysis was executed on the refined range of blade twist angles for 300°, 320°, 340°, 360°, 380°, and 400° degrees. The subscript denotes the impeller geometry and the data type with CFD representing numerical data and EXP representing empirical data. The regression trend lines for each of the three impeller data sets for 6,000, 7,000, and 8,000 RPM were determined to be:

$$\psi_{CFD\ 200} = 4.41\phi^2_{CFD\ 200} - 0.462\phi_{CFD\ 200} + 0.016 \tag{6}$$

$$\psi_{CFD\ 300} = 4.394\phi^2_{CFD\ 300} - 0.493\phi_{CFD\ 300} + 0.021 \tag{7}$$

$$\psi_{CFD\ 400} = 5.972\phi^2_{CFD\ 400} - 0.594\phi_{CFD\ 400} + 0.025 \tag{8}$$

In the refined range of 300° to 400° of blade twist, only a single rotational speed of 6,000 RPM was examined. The regression coefficients for 300° and 400° reflect the different rotational speed used in the calculation. The equations for the refined range of blade twist angles are:

$$\psi_{CFD\ 300} = 4.212\phi^2_{CFD\ 300} - 0.491\phi_{CFD\ 300} + 0.016 \tag{9}$$

$$\psi_{CFD\ 320} = 5.187\phi^2_{CFD\ 320} - 0.525\phi_{CFD\ 320} + 0.022 \tag{10}$$

$$\psi_{CFD\ 340} = 5.271\phi^2_{CFD\ 340} - 0.541\phi_{CFD\ 340} + 0.023 \tag{11}$$

$$\psi_{CFD\ 360} = 5.18\phi^2_{CFD\ 360} - 0.533\phi_{CFD\ 360} + 0.023 \tag{12}$$

$$\psi_{CFD\ 380} = 4.987\phi^2_{CFD\ 380} - 0.538\phi_{CFD\ 380} + 0.024 \tag{13}$$

$$\psi_{CFD\ 400} = 5.859\phi^2_{CFD\ 400} - 0.585\phi_{CFD\ 400} + 0.025 \tag{14}$$

Equations (6), (7), and (8) have different $\beta$ coefficients due to the differing range of rotational speeds evaluated for each set of data. Further details of the regression analysis are available in Table 1. The datasets were evaluated for normality using the Shapiro-Wilks model and were found to be normally distributed within a 95% confidence interval. An F-test was conducted and indicated a strong significance ($p<0.0001$) for the trend lines capturing the effects of the different impeller prototypes in the CFD data. The correlation coefficients ($R^2$ and adjusted $R^2$) for the trend lines were above 0.98 in all cases. A Student t-test indicated the significance for each coefficient in the regression models.

A direct comparison between the impeller designs was made using the regression model coefficients. The impeller having a 400° twist outperformed the impeller with a twist of 300° by an average deviation of 16.7% with a maximum deviation of 19.0% and a minimum deviation of 15.9%. The 400° twist impeller also outperformed the 200° impeller by an average deviation of 44.5% with a maximum deviation of 54.0% and a minimum deviation of 36%. The impeller design that performed most similar to the 400° case was the 380° twisted model. Only an average deviation of 3%, a maximum deviation of 4%, and a minimum deviation of 2.6% was found between the 400° and 380° designs. The other twisted cases at 320°, 340°, and 360° degree levels were determined to have an average deviation of 12.9%, 8.5%, and 7.9%, respectively, in comparison to the 400° twisted impeller.

Blood Damage Analysis

A blood damage analysis was completed for the three cases including the 200°, 300°, and 400° designs at 7,000 RPM and a flow rate of 3 L/min. Table 2 illustrates the results of the blood damage analysis.

TABLE 2

Blood Damage Analysis Results

| CFD Simulation | Mean Residence Time (sec) | Mean Residence Time (sec) | Mean Damage Index (%) | Max Damage Index (%) |
|---|---|---|---|---|
| 200° | 0.55 | 5.4 | 1.60 | 2.00 |
| 300° | 0.35 | 1.97 | 0.43 | 0.68 |
| 400° | 0.35 | 2.17 | 0.16 | 0.28 |

A total of approximately 732 particle streamlines were analyzed.

For the 200° impeller twist case, the mean residence time was 0.55 seconds with a maximum particle residence time of 5.4 seconds. The mean value for the damage index was found to be 1.6% with a maximum value of 2%.

Similarly, for the 300° twist case, the mean residence time was 0.35 seconds with a maximum residence time of 1.97 seconds. The mean value for the damage index was found to be 0.43% with a maximum value of 0.68%.

Figure 11:
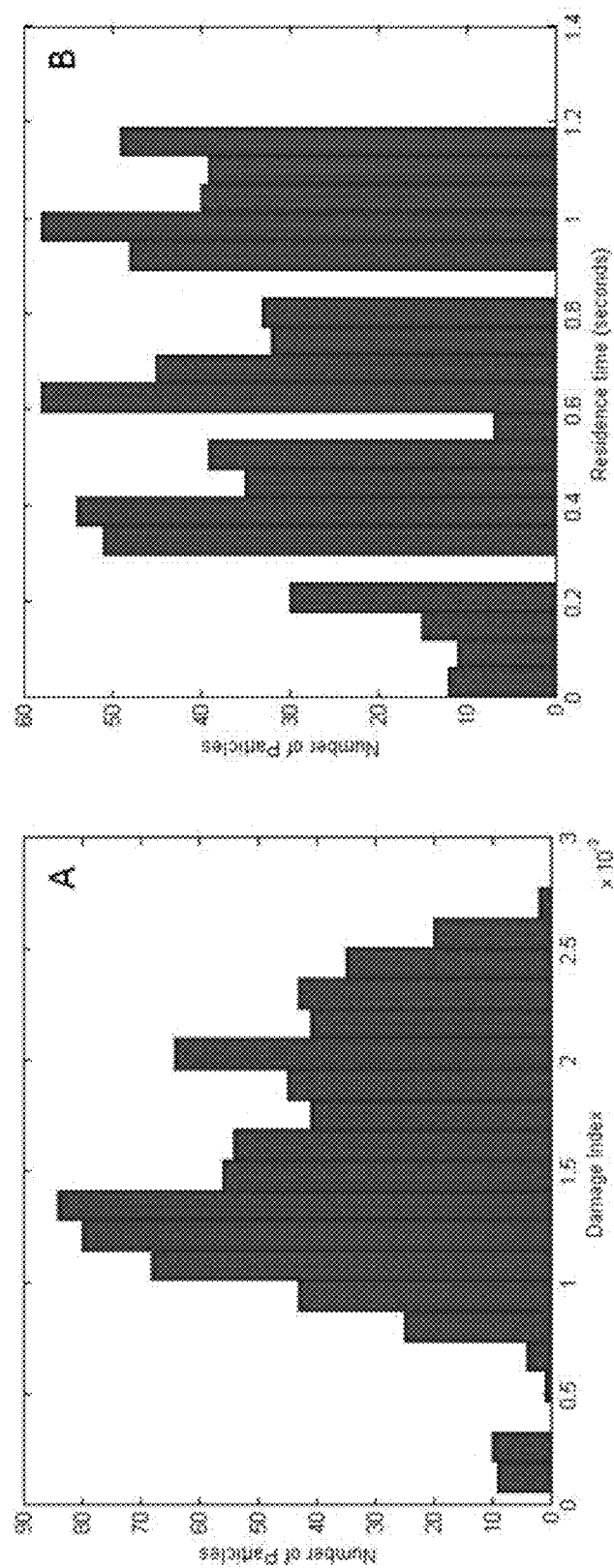
FIG. 11 depicts a blood damage index histogram in Panel (A) and a residence time histogram in Panel (B). Blood damage indices for particles were tracked through the 300° degree impeller for an operating condition of 3 L/min at 7,000 RPM. The mean damage index was 0.16% with a maximum index of 0.28%. The mean residence time was 0.35 seconds with a maximum index of 2.17 seconds.

The results for the 400° design are shown in FIG. 11. The mean residence time was 0.35 seconds with a maximum residence time of 2.17 seconds for the 400° impeller design. The majority of particles took less than 0.42 seconds to pass completely through the model from the inlet through the 400° impeller to the outlet. The mean value for the damage index was found to be 0.16% with a maximum value of 0.28%.

Experimental Hydraulic Testing and Comparison of the 400° Impeller Prototype

In the hydraulic experiments, the fluid properties of the blood analog mixture were measured to be a dynamic viscosity of 3.46+/−0.02 mPa*s and a specific gravity of 1.1+/−0.002. Using this analog fluid, the differential pressure rise across the impeller and the corresponding flow rate for each rotational speed were simultaneously measured. The impeller was able to provide a pressure rise range of 10-31 mmHg over flow rates of 1-4 L/min for rotational speeds of 6,000-8,000 RPM.

Figure 12:
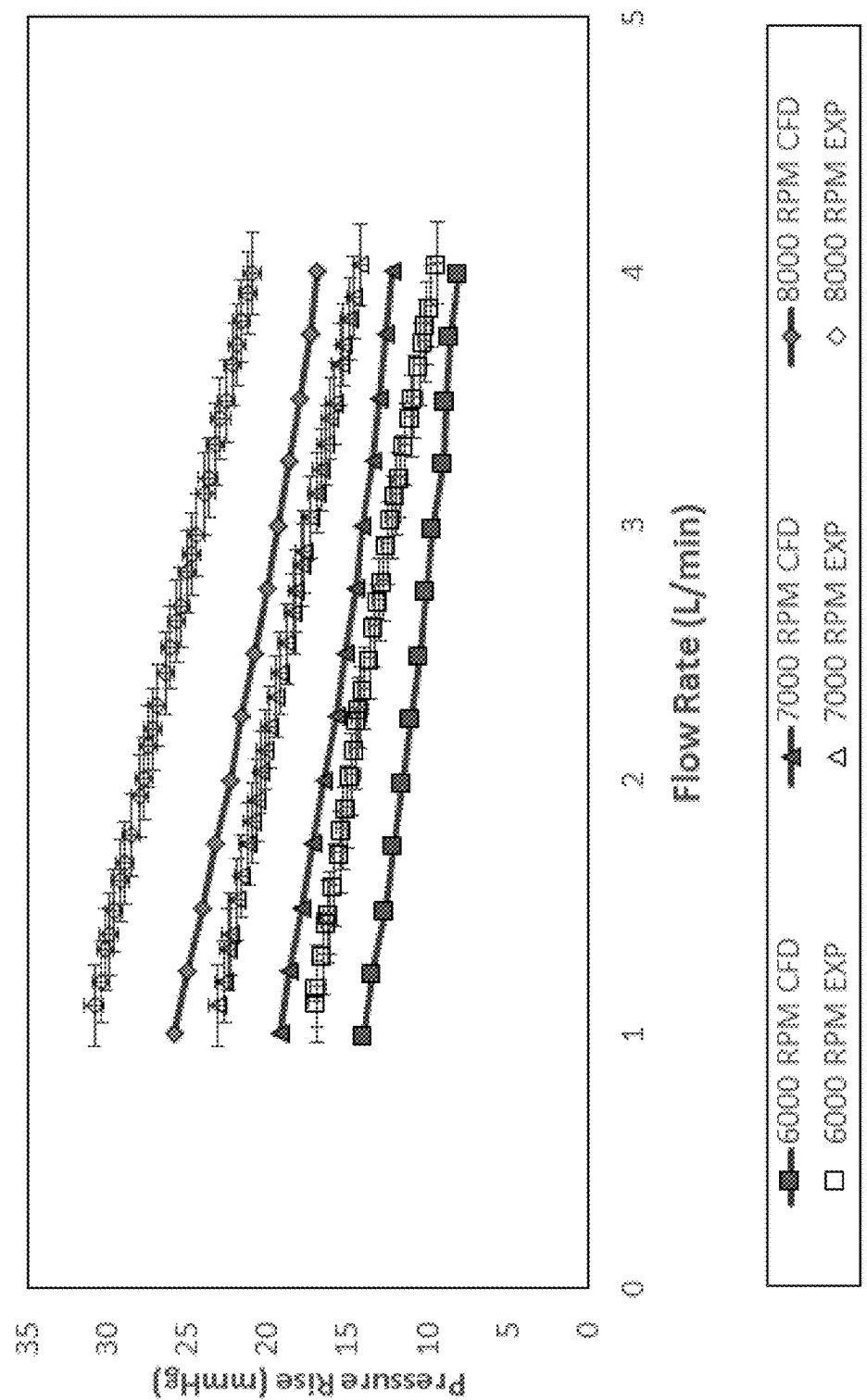
FIG. 12 depicts a comparison of numerical and experimental pump performance curves. The impeller design for 400° of blade twist was evaluated for rotational speeds of 6,000-8,000 RPM.

FIG. 12 depicts a comparison between the numerical and experimental performance curves. The regression trend line for the experimental data was determined to be:

$$\psi_{EXP\ 400} = -0.464 \phi_{EXP\ 400} + 0.028 \quad (15)$$

Table 1 also lists the non-dimensional coefficients and statistical $R^2$ and adjusted $R^2$ values above 0.99 for the regression model. The average and maximum deviation between the CFD predictions and experimental measurements were determined to be 15% and 21%, respectively.

Discussion

The total cavopulmonary connection (TCPC) is an imperfect treatment solution for those patients with single ventricle physiology. A univentricular heart has a single functioning ventricle to power the systemic circulation without a way to generate a pressure rise for the pulmonary circulation. Despite advances in surgical techniques, surgical planning, and pharmacological therapy, patients continue to experience late stage pathophysiologies occurring in the months to several years after the Fontan surgery. Mechanical circulatory support in the form of cavopulmonary assist provides a means of supplementing venous return flow to the left atrium.

Applicant describes a percutaneously-inserted axial flow blood pump for use as a cavopulmonary assist device. The device is intended to provide at least 4 weeks of temporary mechanical circulatory support with the pump being exchanged for extended term support. This study initially examined 6 impeller geometries with varying blade twist angles between 100° and 600° using computational fluid dynamics simulations. After positive results were obtained, 4 additional prototype impellers were examined in the range of 300° and 400° of blade angle twist in 20° increments in order to zero in on an optimal blade twist angle. The results of the optimized impeller design include pressure generation studies with the optimal design being validated with a hydraulic test. Additional numerical analyses including a quasi-steady state analysis determined the optimal blade tip angle for the maximum pressure rise. A blood damage analysis was performed in order to assess the probability of blood trauma. A comparison of the impeller prototypes was performed using a non-dimensional, statistical regression analysis.

Through the iterative design process using CFD, the optimal impeller geometry was found to be the 400° impeller. The numerical model was able to generate 1-4 L/min with pressure rises of 4-26 mmHg for rotational speeds of 6,000-8,000 RPM. The prototype of the 400° impeller was able to generate a similar performance with pressure rises of 10-31 mmHg for flow rates of 1-4 L/min at 6,000-8,000 RPM. The numerical model and the hydraulic test were in reasonable agreement. The maximum deviation was determined to be 21% between the numerical and experimental data sets, which is typical of such a comparison due to limitations of CFD simulations. The quasi-steady state study of the 400 degree impeller was performed to determine the optimum blade twist angle for pressure generation. The results showed that the pressure rise remained reasonable between 13.75 and 14.15 mmHg. Significant variations in pressure generation were not found in the quasi-steady analysis results. Sources that contribute to this deviation include different fluid properties, modeling limitations due to turbulence model, and computational rounding.

In consideration of the blood damage analysis, the damage indices were within acceptable levels. The maximum damage index was found to be quite low for the 200° model. The maximum damage index for the 300° model was 0.68%. The blood damage analysis showed that the 400° impeller had 0.28% maximum damage index. In general, the mean damage indices under all of the operating conditions were found to be less than the target value of 2%, which is encouraging. The maximum damage indices never exceeded 2%. As a comparison, clinically available blood pumps may have blood damage indices in the range of 4-6%.

Conclusion

There has been limited advancement in the development of the blood pumps for cardiac patients (e.g., patients having congestive heart failure or Fontan physiologies) and those with complex congenital heart disease. This study promotes further development of new impeller designs for incorporation into a new axial flow blood pump for cardiac patients. Computational fluid dynamics simulations were conducted to study the separate impeller designs with a range of 100° to 600° of blade twist. Numerical analyses included a quasi-steady study and a blood trauma analysis. Experimental testing validated the computational predictions to within 21%. Applicant found significant results that will be used in future design iterations of the impellers.

Further Impeller Geometries

Figure 13:
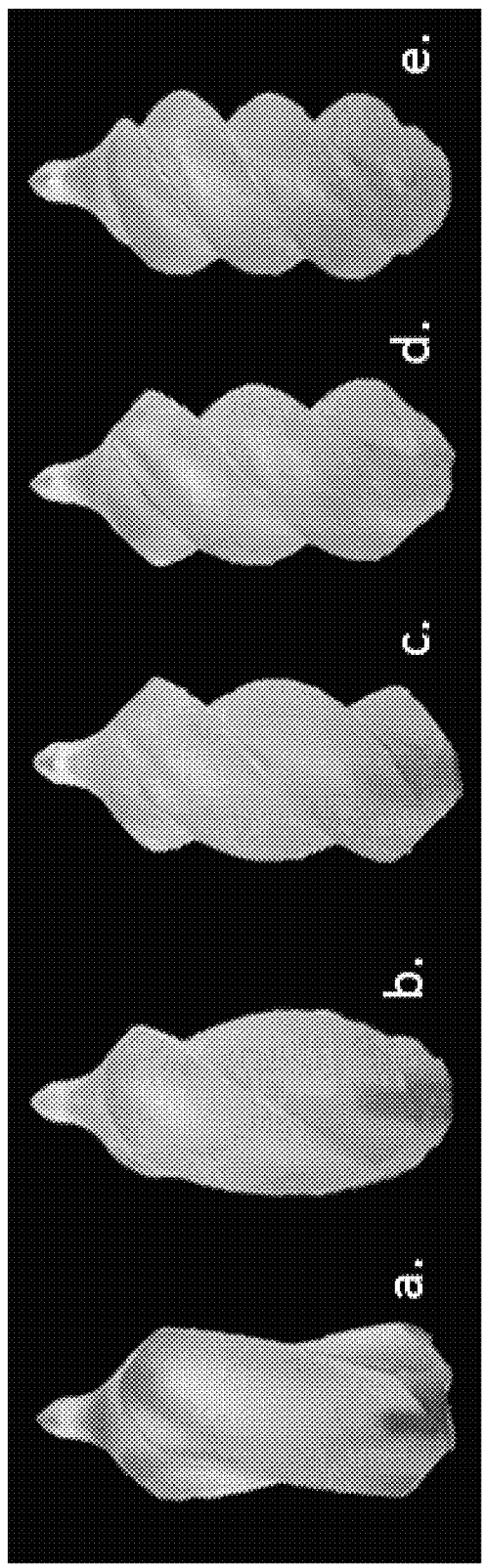
FIG. 13 depicts "T-type" cavopulmonary impeller designs. Panels (a), (b), (c), (d), and (e) depict impellers with 100°, 200°, 300°, 400°, and 500° of blade twist, respectively.
Figure 14:
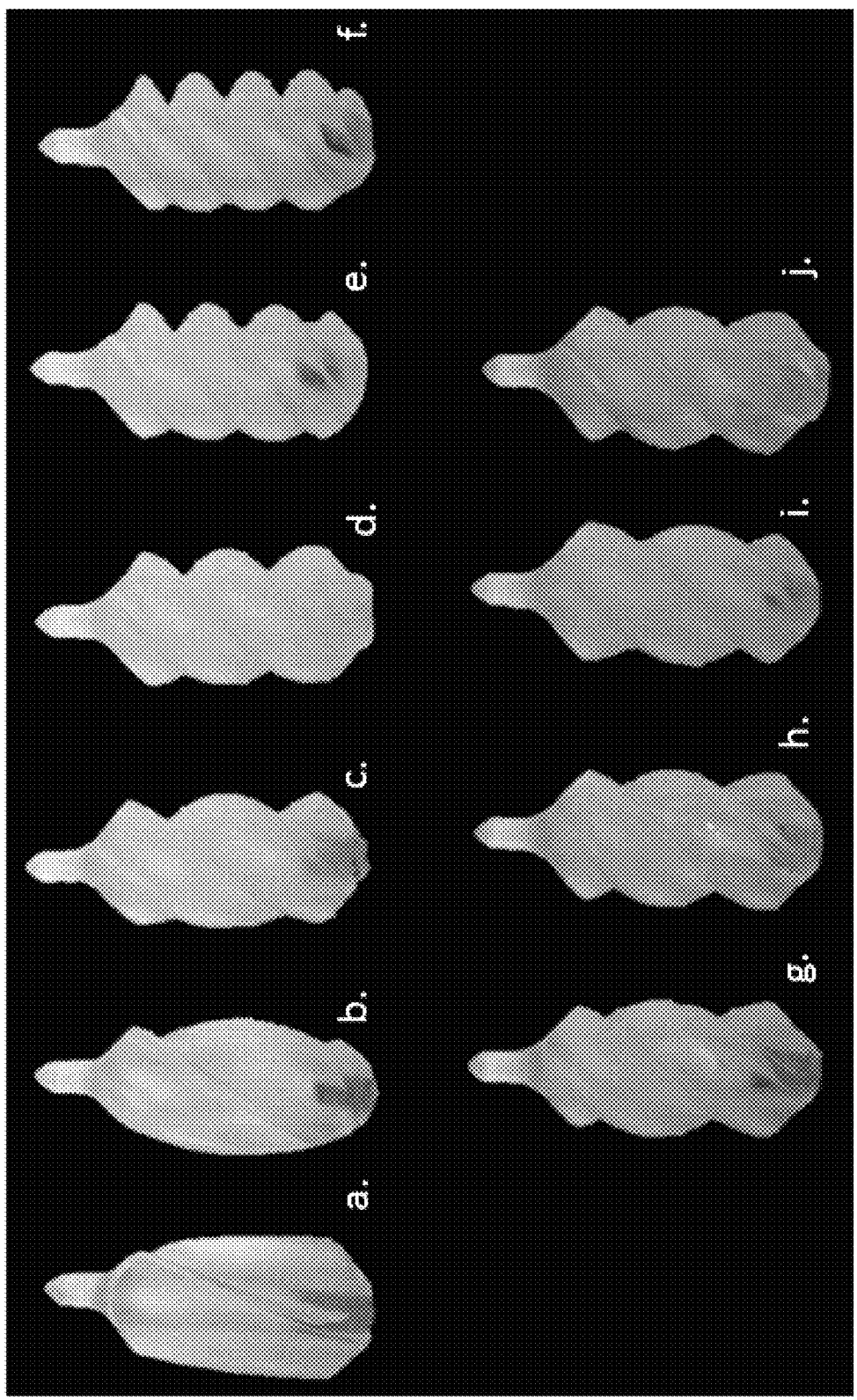
FIG. 14 depicts "0-type" cavopulmonary impeller designs. Panels (a), (b), (c), (d), (e), (f), (g), (h), (i), and (j) depict impellers with 100°, 200°, 300°, 400°, 500°, 600°, 320°, 340°, 360°, and 380° of blade twist, respectively.

Applicant utilized three-dimensional computer aided design (CAD) software (SolidWorks 2014, Dassault Systems, Concord, Mass.) to generate the impeller designs in this study. Applicant initially developed 5 axial-flow impeller geometries and modified the angle of twist or pitch of the impeller blades from 100° to 500° at 100° increments illustrated in FIG. 13. These impellers are referred to as "T-type" prototypes that were developed based off of pump design principles. The T-type impellers were optimized for pressure generation to create a set of "O-type" impellers. The O-type impellers had blade twist angles of 100° to 600°. Applicant also refined the design with focused iterations between 300° and 400° of blade twist at 20° increments. FIG. 14 displays the impeller prototypes. The differences between the T-type and O-type impellers include modifying the angle of twist for the impeller blades, varying the length and height of the blades, as well as modifying the shape and diameter of the impeller hub. Table 3 displays the physical dimensions of the impellers.

TABLE 3

Impeller Design Characteristics for the Prototype Impellers

| Design Characteristic Prototype | Dimensions T-Type | Dimensions O-Type |
|---|---|---|
| Number of Blades | 4 | 4 |
| Range of Twist Angles (degrees) | 100-500 | 100-600 |
| Impeller Diameter (mm): Mean Value (Range) | 14.5 (+/− 0.3) | 14.3 (+/− 0.3) |
| Blade Height (mm): Mean Value (Range) | 4.2 (+/− 0.7) | 4.3 (+/− 1.4) |
| Blade Thickness (mm): Mean Value (Range) | 2.0 (+/− 0.2) | 1.72 (+/− 0.4) |
| Length (mm): Mean Value (Range) | 34.5 (+/− 0.6) | 36.4 (+/− 0.5) |

Stereolithography (SLA) manufacturing of the prototypes using WATERSHED® XC11122 resin was executed by Applied Rapid Technologies of Fredericksburg, Va. A shaft- or flexible-cable-driven configuration was employed to evaluate the hydraulic performance of impeller prototypes.

Hydraulic Flow Loop

The experimental set depicted in and described in the context of FIG. 5 was utilized for hydraulic experiments. A Cannon-Fenske routine viscometer and a hydrometer were used to verify the fluid properties to produce a solution with a dynamic viscosity of 3.46+/−0.02 mPa*s and a specific gravity of 1.1+/−0.002. During hydraulic testing, the ultrasonic flow probe was used to measure the flow in the TYGON® tubing, while the pinch valve was used to increase or decrease the resistance to flow in the tubing. The pressure sensor and flow meter were calibrated prior to any experiments taking place. Simultaneous measurements of the flow rate and pump pressure rise were collected using LABJACK® software at a sampling rate of 100 Hz. The pump was tested at 4 different operating speeds collecting 40 sample points.

Regression Analysis

Non-dimensional regression analysis was performed in order to internally compare the impeller hydraulic performance across individual impeller prototypes as described in Throckmorton 2007. The discrete data points for pressure and flow were condensed into two non-dimensional coefficients for each prototype tested for the three rotational speeds evaluated. The coefficients are represented described in the context of Equations (3) and (4) herein.

The pressure and flow coefficients were calculated and displayed on each scatter plot. A regression analysis was then performed on both data sets by fitting a polynomial regression model. The pressure and flow data points were used to calculate a pressure coefficient and a flow coefficient. The coefficients for each predicted data point are plotted on an X-Y scatter plot and a 1st order polynomial regression model was fitted to each set of results. The statistical regression model is displayed in Equation (16) below describing the characteristic constants ($\beta_0$, $\beta_1$), where the subscript type references the impeller prototype.

$$\Psi_{type}=\beta_1(\Phi_{type})+\beta_0 \quad (16)$$

An F test was performed on the regression analysis in order to determine the statistical significance of the coefficients and the polynomial models. This statistical analysis was performed for all prototype impellers to obtain separate mathematic expressions for each one. The regression analysis was repeated for each case and a separate mathematical expression was obtained. A comparison was made between the individual impeller cases and used to evaluate the hydraulic performance of each prototype impeller against each other.

Results

Pressure Generation

The studies examined the pressure rise across 3 experimental sets of prototype impellers with varying angles of blade twist for rotational speeds of 6,000-8,000 RPM for flow rates of 1-5 L/min. Three separate studies were executed with significantly modified prototypes in each experimental set.

Figure 15:
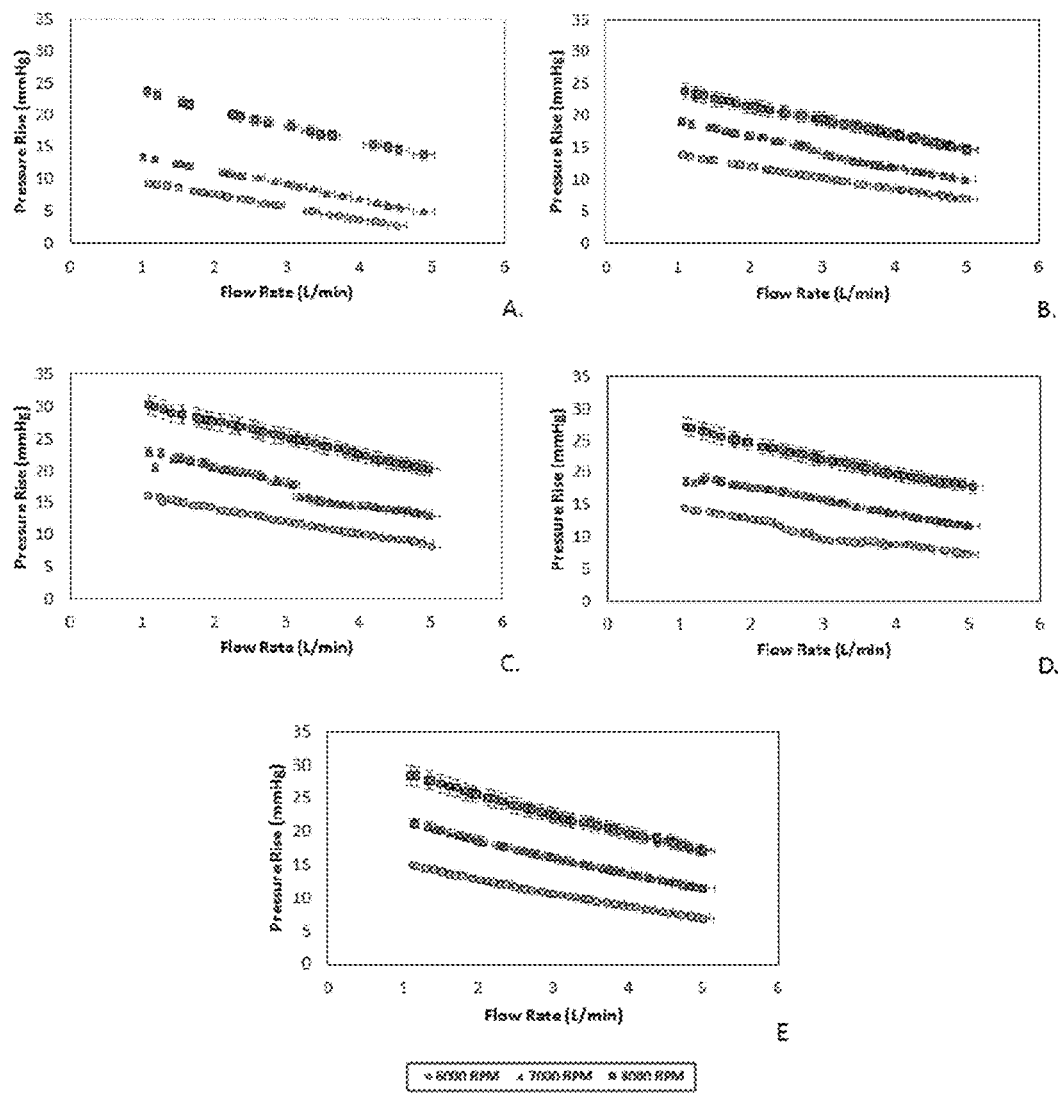
FIG. 15 depicts a comparison of pump performance curves for T-type impeller designs according to embodiments of the invention. Panels (A), (B), (C), (D), and (E) depict results for impellers with 100°, 200°, 300°, 400°, and 500° of blade twist, respectively. The impellers were evaluated at a rotational speeds of 6,000-8,000 RPM over a flow range of 1-5 L/min.

The initial study looked at the T-type impellers with blade twist angles of 100°-500° at a rotational speed range of 6,000-8,000 RPM. The results are illustrated in FIG. 15. The T-type impellers were able to generate pressure rises of 3-30 mmHg. The T300 impeller had the largest pressure rise for 8-30 mmHg for flow rates of 1-5 L/min.

Figure 16:
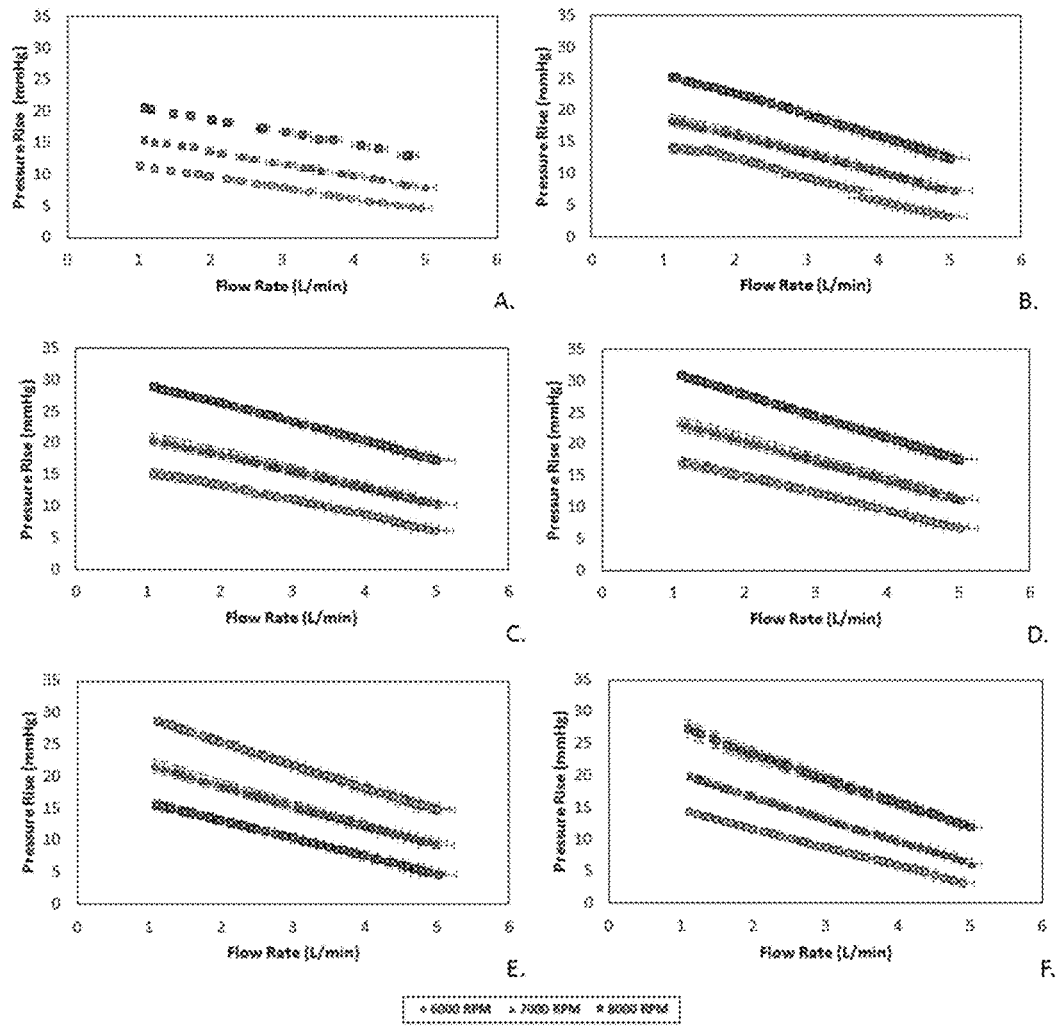
FIG. 16 depicts a comparison of performance curves for optimized impeller designs according to an embodiment of the invention. Panels (A), (B), (C), (D), (E), and (F) depict results for impellers with 100°, 200°, 300°, 400°, 500°, and 600° of blade twist, respectively. The impellers were evaluated at rotational speeds of 6000-8000 RPM over a flow range of 1-5 L/min.

The second study examined the O-type prototypes with blade twist angles between 100° and 600° of twist. The results for the O-type impeller are illustrated in FIG. 16. These impellers were able to generate pressure rises of 3-31 mmHg. The O400 impeller had the largest pressure rise of 7-31 mmHg for flow rates of 1-5 L/min.

Figure 17:
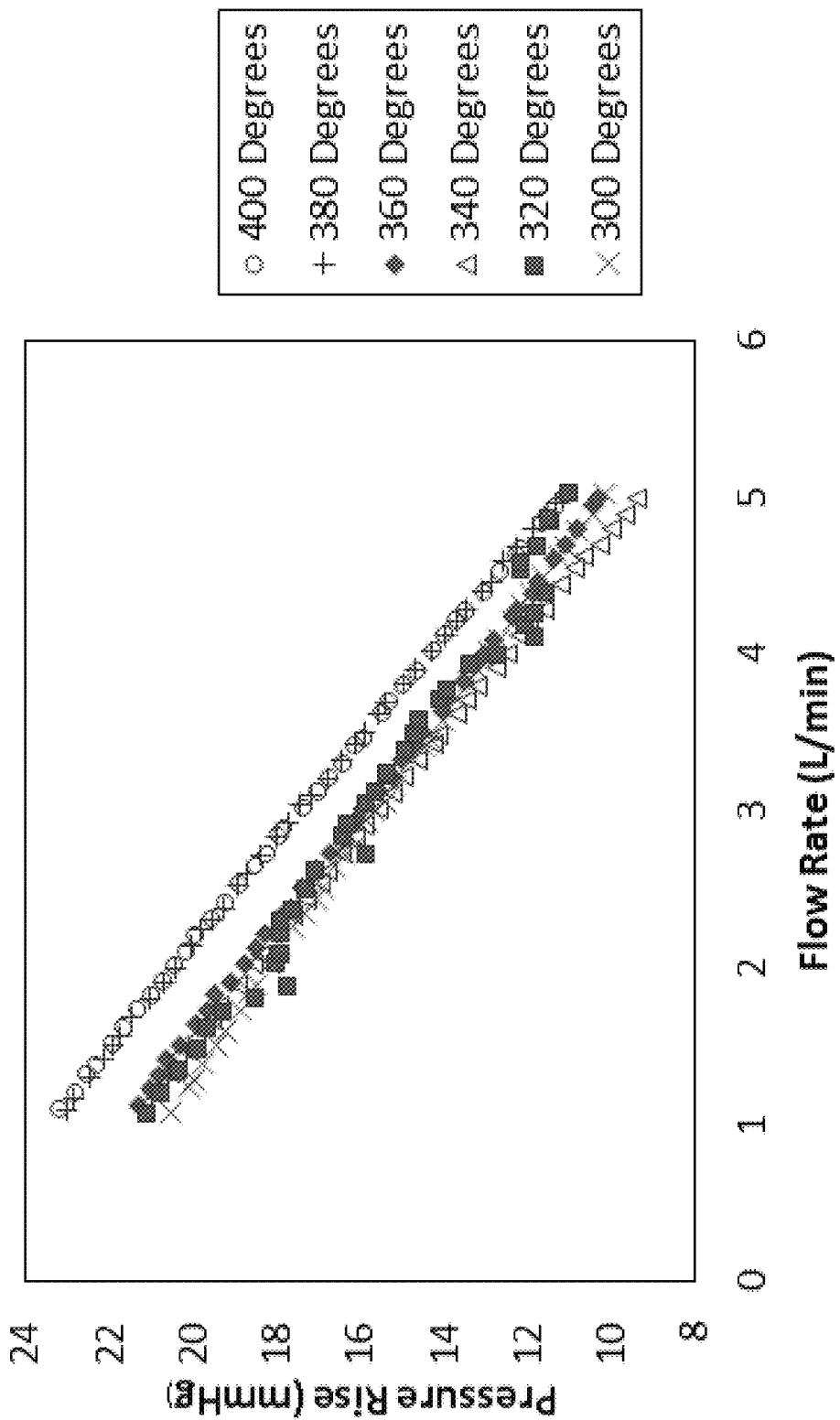
FIG. 17 depicts performance curves for optimized impellers according to embodiments of the invention in the range of 300°-400° in 20° degree increments for a rotational speed of 7,000 RPM.

A third study examined an experimental study of a refined range of blade twist angles for a range of angles between 300 and 400 degrees of twist in 20° increments. The results of these experiments are shown in FIG. 17 for a rotational speed of 7,000 RPM proved that a small increase in blade twist angle is able to significantly affect the pressure generation of the pump prototype. The O400 impeller geometry generated the largest pressure rise in the study.

Statistical Analysis of Prototype Impellers

A regression analysis was carried out on all three experimental data sets including the pump prototypes for the T-type prototypes with 100°-500° of blade twist, the O-type prototypes with 100°-600° of blade twist, and the refined range with 300°, 320°, 340°, 360°, 380°, and 400° degrees of blade twist. The values for the characteristic constants for each statistical result are displayed in Table 4.

TABLE 4

Polynomial Regression Analysis of Numerical Predictions for the Prototype Impellers

| Type | $\beta_1$ | p | $\beta_0$ | p | F-test | $R^2$ | $R^2_{adj}$ |
|---|---|---|---|---|---|---|---|
| T100° | −0.345 | <.0001 | 0.017 | <.0001 | <.0001 | 0.985 | 0.985 |
| T200° | −0.309 | <.0001 | 0.021 | <.0001 | <.0001 | 0.957 | 0.956 |
| T300° | −0.375 | <.0001 | 0.026 | <.0001 | <.0001 | 0.967 | 0.966 |
| T400° | −0.329 | <.0001 | 0.023 | <.0001 | <.0001 | 0.965 | 0.965 |
| T500° | −0.385 | <.0001 | 0.025 | <.0001 | <.0001 | 0.993 | 0.993 |
| O100° | −0.301 | <.0001 | 0.018 | <.0001 | <.0001 | 0.994 | 0.994 |
| O200° | −0.483 | <.0001 | 0.024 | <.0001 | <.0001 | 0.979 | 0.979 |
| O300° | −0.417 | <.0001 | 0.025 | <.0001 | <.0001 | 0.975 | 0.975 |
| O400° | −0.464 | <.0001 | 0.028 | <.0001 | <.0001 | 0.993 | 0.993 |
| O500° | −0.485 | <.0001 | 0.026 | <.0001 | <.0001 | 0.999 | 0.999 |
| O600° | −0.519 | <.0001 | 0.025 | <.0001 | <.0001 | 0.997 | 0.997 |
| O320° | −0.439 | <.0001 | 0.025 | <.0001 | <.0001 | 0.971 | 0.971 |
| O340° | −0.473 | <.0001 | 0.026 | <.0001 | <.0001 | 0.994 | 0.994 |
| O360° | −0.448 | <.0001 | 0.026 | <.0001 | <.0001 | 0.997 | 0.997 |
| O380° | −0.475 | <.0001 | 0.028 | <.0001 | <.0001 | 0.992 | 0.992 |

The regression trend lines for each dataset were determined to be:

$$\psi_{T100} = -0.345 \phi_{T100} + 0.017 \quad (17)$$

$$\psi_{T200} = -0.309 \phi_{T200} + 0.021 \quad (18)$$

$$\psi_{T300} = -0.375 \phi_{T300} + 0.026 \quad (19)$$

$$\psi_{T400} = -0.329 \phi_{T400} + 0.023 \quad (20)$$

$$\psi_{T500} = -0.385 \phi_{T500} + 0.025 \quad (21)$$

The following equations are for the optimized impeller:

$$\psi_{O100} = -0.301 \phi_{O100} + 0.018 \quad (22)$$

$$\psi_{O200} = -0.483 \phi_{O200} + 0.024 \quad (23)$$

$$\psi_{O300} = -0.417 \phi_{O300} + 0.025 \quad (24)$$

$$\psi_{O400} = -0.464 \phi_{O400} + 0.028 \quad (25)$$

$$\psi_{O500} = -0.519 \phi_{O600} + 0.025 \quad (26)$$

The equations for the refined range of blade twist angles are:

$$\psi_{O320} = -0.439 \phi_{O320} + 0.025 \quad (22)$$

$$\psi_{O340} = -0.473 \phi_{O340} + 0.026 \quad (23)$$

$$\psi_{O360} = -0.448 \phi_{O360} + 0.026 \quad (24)$$

$$\psi_{O380} = -0.475 \phi_{O380} + 0.028 \quad (25)$$

All datasets were evaluated for normality using the Shapiro-Wilks model and were found to be in a normal distribution within a 95% confidence interval. An F-test was conducted and indicated a strong significance (p<0.0001) for the trend lines capturing the effects of the different impeller prototypes in the data. The correlation coefficients ($R^2$ and adjusted $R^2$) for the trend lines were above 0.95 in all cases. A Student t-test was performed on each of the regression coefficients and indicated the significance for each coefficient in the regression models.

Adjustable Pitch Impellers

Figure 18A:
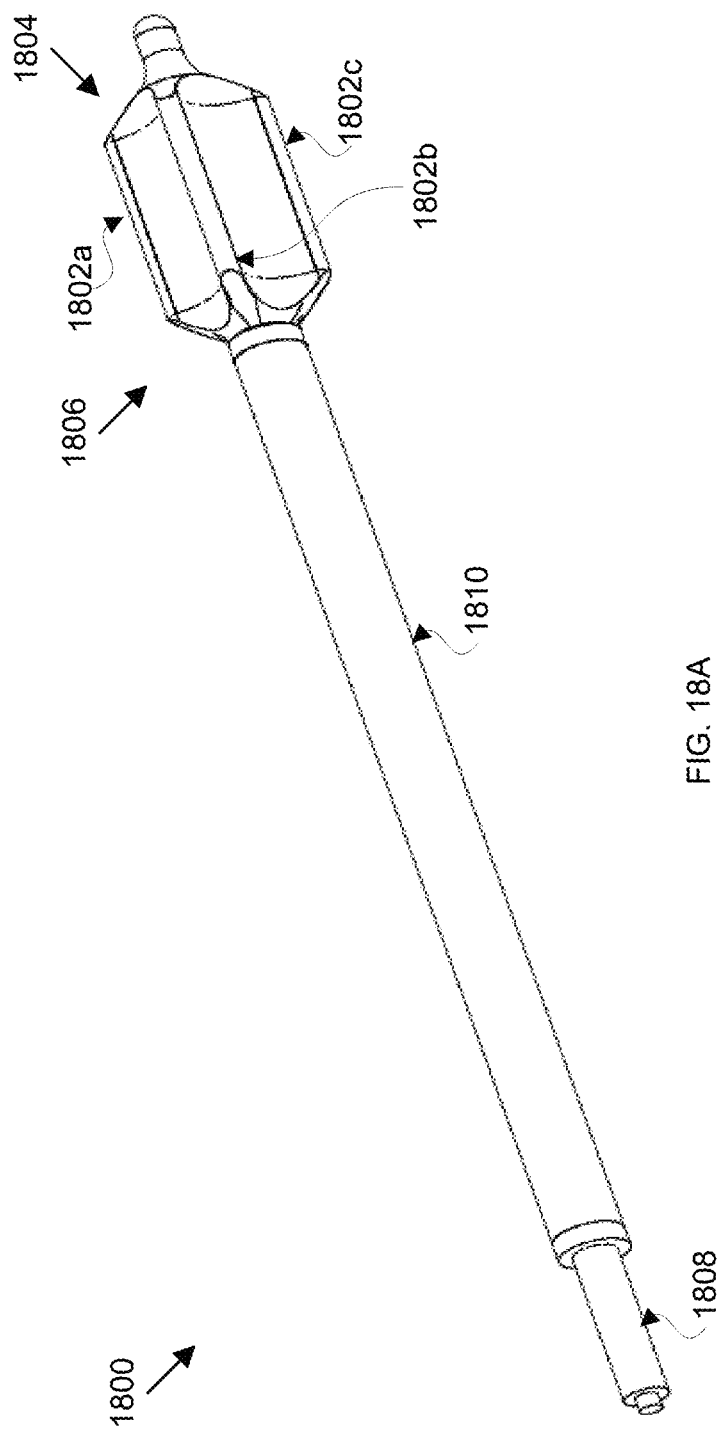
FIGS. 18A-18F depict an adjustable impeller according to an embodiment of the invention for infants, children, adolescents, and adults with heart failure secondary to acquired or congenital heart disease.
Figure 18B:
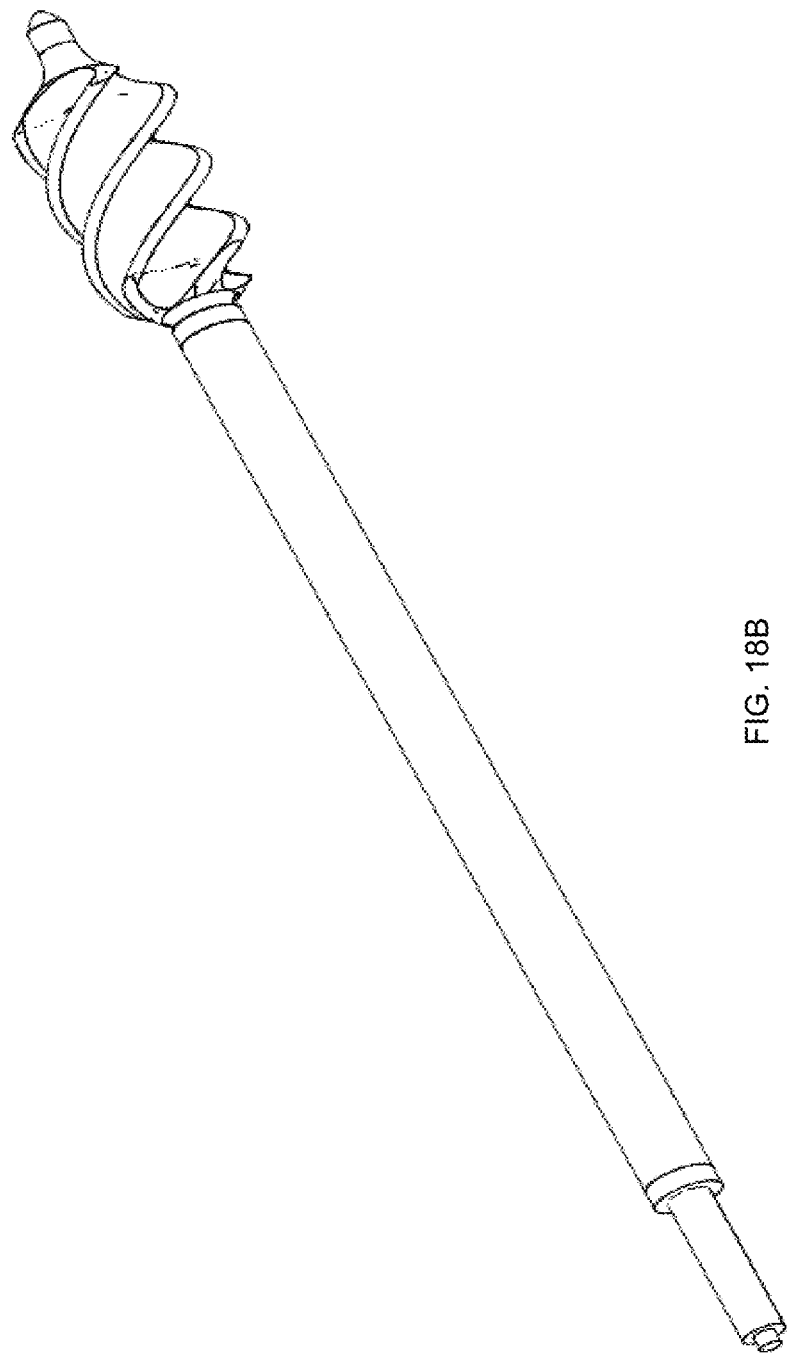

Referring now to FIGS. 18A and 18B, another aspect of the invention provides an adjustable pitch impeller 1800 that allows for adjustment of the blade pitch to an optimal value for a given patient and/or rotational speed. Embodiments of the invention are capable of both wide ranges of twist angles as well as fine resolution (e.g., to the nearest 20°, to the nearest 15°, to the nearest 10°, to the nearest 5°, to the nearest 1°, to the nearest 0.1°, to the nearest 0.01°, to the nearest 0.001°, to the nearest 0.0001°, and the like).

In some embodiments of the invention, the blades are formed with a pre-twist of a desired angle (e.g., 200°), but can be rotated to either further twist or untwist the blades. For example, the pre-twisted blade can be untwisted to 0°, further twisted to 2880° (i.e., 8 revolutions), or any degree of twist in between. Pre-twisting can minimize the rotation necessary to achieve a desired twist for a particular physiological situation.

Impeller 1800 can include a plurality of blades 1802a-1802c (a fourth blade is hidden from view). Blades 1802 can be formed from a flexible, biocompatible polymer, which can optionally be molded over a frame. In some embodiments, the frame and/or the polymer have shape memory. For example, the frame can be made from a Nitinol alloy or a Nitinol alloy coated with a biocompatible polyurethane film.

The pitch of the blades 1802 can be adjusted by rotating a first end 1804 of the blades relative to a second end 1806 of the blades. Rotational force can be imparted by a coaxial shaft or flexible cable arrangement including an internal shaft/cable 1808 and an external shaft/cable 1810. Each shaft 1808, 1810 can be coupled to one end 1804, 1806 of the blades 1802 so that rotation of one shaft 1808, 1810 while the other shaft 1810, 1808 is either held stationary or rotated in the opposite direction will twist the blades 1802.

Figure 18C:
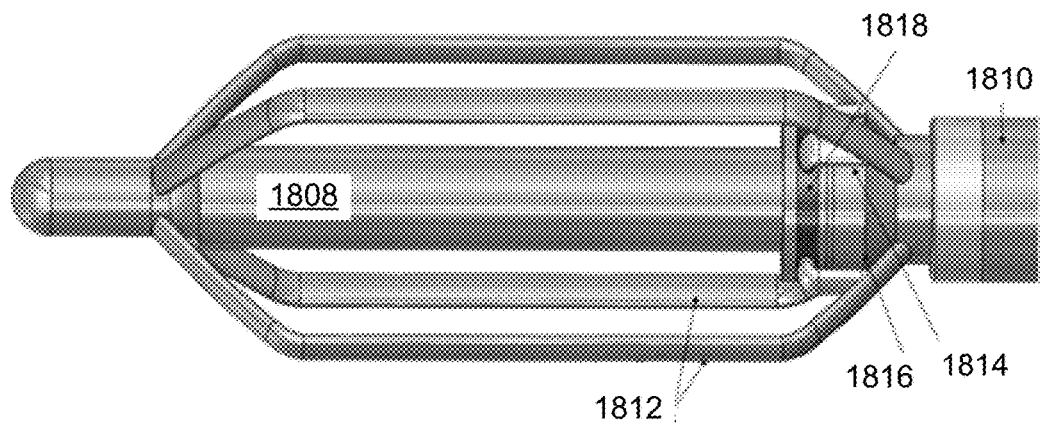
Figure 18D:
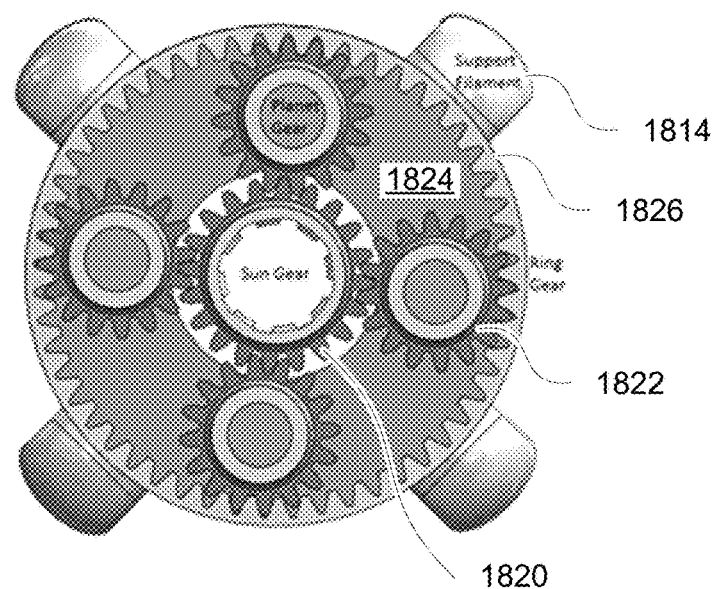
Figure 18E:
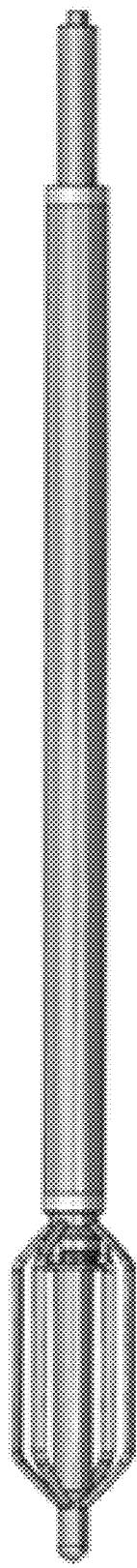
Figure 18F:
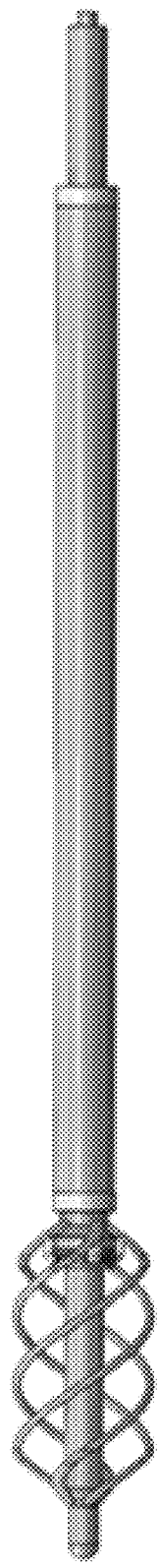
Figure 19:
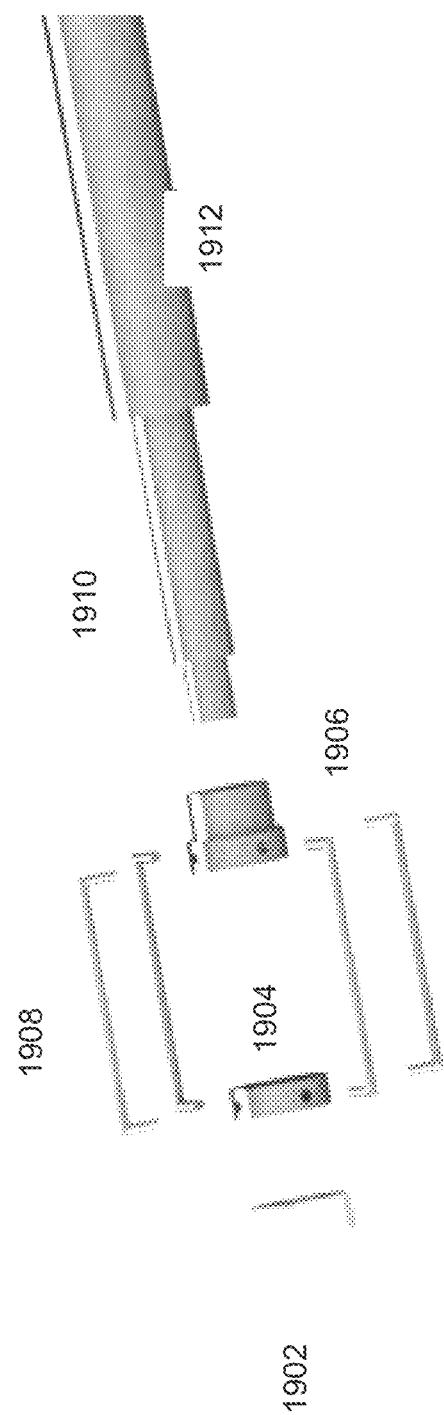
FIG. 19 provides an exploded view of an impeller according to an embodiment of the invention including an acorn nut 1902, a top hub 1904, a bushing 1906, Nitinol wires 1908, an inner rod 1910, and an outer tube 1912.

In some embodiments, the impeller 1800 can include one or more gears to produce mechanical advantage to achieve a desired speed and/or torque. For example, as depicted in FIGS. 18C and 18D, the internal shaft 1808 and/or filaments 1812 for blades 1802 can be rotationally coupled to one or more of the sun gear 1820, the orbital gears 1822, the orbital carrier 1824, and the ring gear 1826 of a planetary (also known as epicyclic) gearing system 1818 to transmit rotation to the distal end 1804 of the blades 1802. In one embodiment, the gearing lies inside of the frame and polymer. For example, in the embodiment depicted in FIGS. 18C and 18D, the internal shaft 1808 is coupled to the sun gear 1820 and further extends beyond the sun gear 1820 to couple to the first end 1804 of the blades 1802. The orbital gears 1822 are held stationary (e.g., by coupling of the planetary carrier 1824 to the external shaft 1810) and the ring gear 1826 is coupled to the second end 1806 of the blades 1802, e.g., via connecting filaments 1814. As the internal shaft 1808 is rotated, the first end 1804 and the second end 1806 of the blades 1802 will rotate at different rates due to the presence of the planetary gearing system 1818 at the second end 1806 of the blades 1802, thereby producing twist in the blades 1802. A ball screw 1816 can advance and retract as the internal shaft is rotated to accommodate the shortening and lengthening of blades 1802 as they are twisted.

Additionally or alternatively, one or more piezoelectric and/or electroactive polymers that can flex to a desired orientation in response to application of electricity to the blades can be utilized. In another embodiment, the piezoelectric and/or electroactive polymers can be utilized to generate electricity as strain is imparted on the polymer during rotation of the impeller. The generated electricity can be utilized to power a motor to turn the impeller.

Passive flexible materials, such as biocompatible polyurethane, could be incorporated into the structure of components to deform in an expected and controlled manner such as to pitch in a way that enhances energy transfer. The blade number and height can vary using these materials to generate the desired hydraulic performance for the impeller. A combination of shorter rigid blades could also be coupled with a certain number of actively-twisted (gears, magnets, electroactive polymers, or piezoelectric materials) or passive (flexible materials) pitch-adjustive blades to create the optimal impeller geometry for either pulmonary or systemic circulatory support conditions.

Moreover, the gear system and/or impeller end can be rapidly exchanged for another pitched impeller design to satisfy the pressure and flow needs for each patient individually or as a patient's hemodynamic status changes or as the patient grows and develops from infancy into childhood. In this case, the impeller design is different, but the drive system is common.

Given a known blade length in an untwisted state, a user can control the twist angle of the shafts 1808, 1810 relative to each other in order to achieve a desired pitch. Various combinations of twist angles, blade lengths, and associated pitch are depicted in Table 5 below.

TABLE 5

| Twist Angle (°) | Impeller Length (mm) | Pitch (°/mm) | Impeller Length (mm) | Pitch (°/mm) |
|---|---|---|---|---|
| 100 | 34 | 2.9 | 36 | 2.8 |
| 120 | 34 | 3.5 | 36 | 3.3 |
| 140 | 34 | 4.1 | 36 | 3.9 |
| 160 | 34 | 4.7 | 36 | 4.4 |
| 180 | 34 | 5.3 | 36 | 5.0 |
| 200 | 34 | 5.9 | 36 | 5.6 |
| 220 | 34 | 6.5 | 36 | 6.1 |
| 240 | 34 | 7.1 | 36 | 6.7 |
| 260 | 34 | 7.6 | 36 | 7.2 |
| 280 | 34 | 8.2 | 36 | 7.8 |
| 300 | 34 | 8.8 | 36 | 8.3 |
| 320 | 34 | 9.4 | 36 | 8.9 |
| 340 | 34 | 10.0 | 36 | 9.4 |
| 360 | 34 | 10.6 | 36 | 10.0 |
| 380 | 34 | 11.2 | 36 | 10.6 |
| 400 | 34 | 11.8 | 36 | 11.1 |
| 420 | 34 | 12.4 | 36 | 11.7 |
| 440 | 34 | 12.9 | 36 | 12.2 |
| 460 | 34 | 13.5 | 36 | 12.8 |
| 480 | 34 | 14.1 | 36 | 13.3 |
| 500 | 34 | 14.7 | 36 | 13.9 |
| 520 | 34 | 15.3 | 36 | 14.4 |
| 540 | 34 | 15.9 | 36 | 15.0 |
| 560 | 34 | 16.5 | 36 | 15.6 |
| 580 | 34 | 17.1 | 36 | 16.1 |
| 600 | 34 | 17.6 | 36 | 16.7 |
| 620 | 34 | 18.2 | 36 | 17.2 |
| 640 | 34 | 18.8 | 36 | 17.8 |
| 660 | 34 | 19.4 | 36 | 18.3 |
| 680 | 34 | 20.0 | 36 | 18.9 |
| 700 | 34 | 20.6 | 36 | 19.4 |

Shafts 1808, 1810 can be rotated and held in a desired rotational position through a variety of techniques and devices. In one embodiment, the shafts 1808, 1810 can be manually twisted. In another embodiment, motors (e.g., compact, micro, and/or servomotors) and/or gearing can be utilized to rotate the shafts 1808, 1810 and/or hold them in place. Such an embodiment can enable real-time adjustment of the pitch while the impeller is rotated in situ. In still other embodiments, one or more magnets can be utilized to hold the shafts 1808, 1810 in place. Other means for holding the shafts 1808, 1810 in a desired rotational arrangement include screws (e.g., set screws, thumb screws, and the like), collets, and pinching arrangements such as described in U.S. Patent Application Publication Nos. 2007/0118079 and 2012/0078232. Various bearings including ball bearings, needle bearings, magnetic bearings, and the like can be utilized to support and facilitated movement of various components. Exemplary magnetic bearings are described in U.S. Pat. Nos. 5,347,190; 5,355,042; 6,074,180; 6,394,769; 6,595,762; 7,070,398; 7,229,258; and 7,462,019.

The components described herein can be assembled in a modular manner so that various components can be quickly replaced before reinsertion and percutaneous placement of the devices.

Single Body Design

Figure 20A:
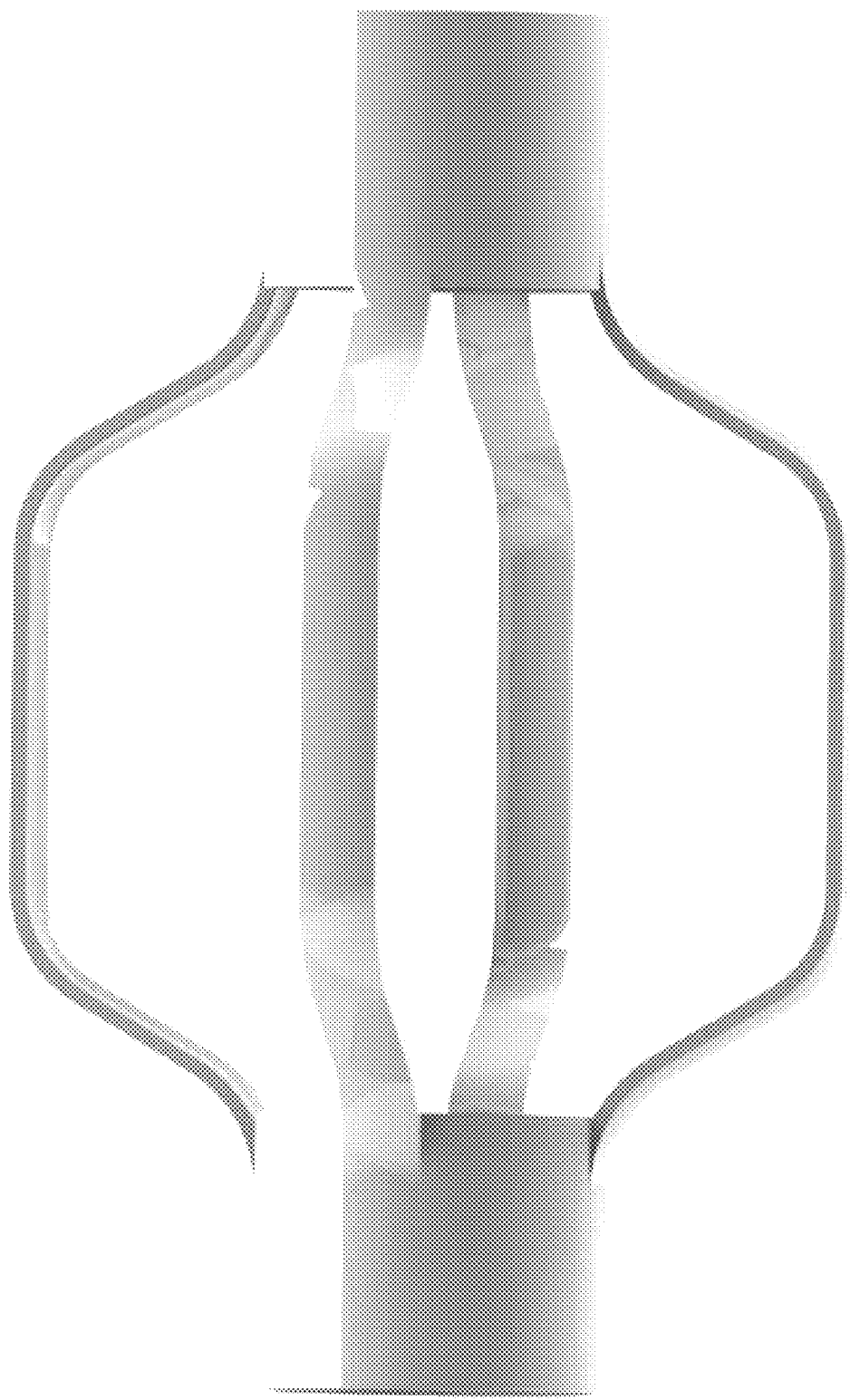
FIGS. 20A and 20B depicts an exemplary single body design in which wires 1908 are formed by removing material from Nitinol tubing according to an embodiment of the invention.
Figure 20B:
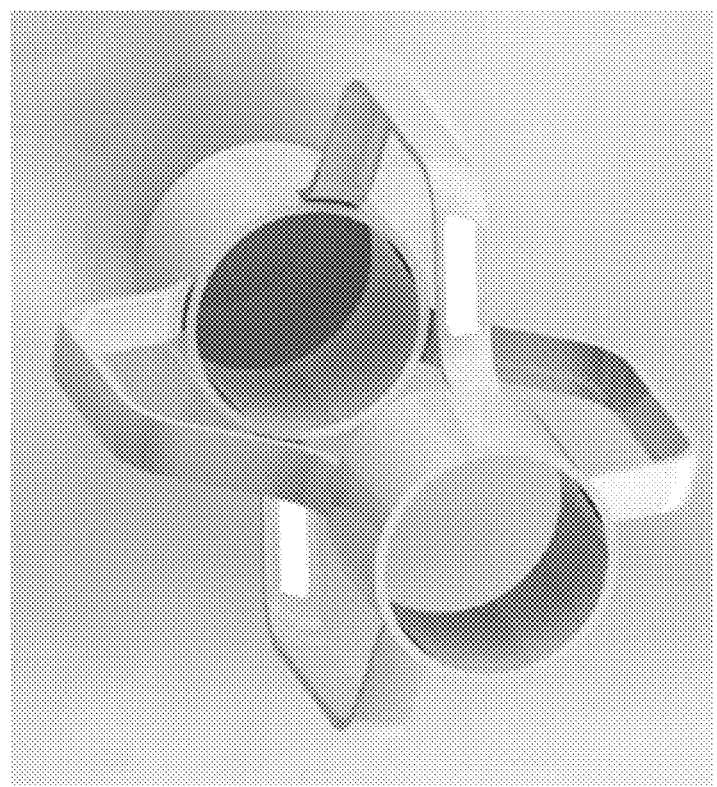

One embodiment of the invention utilizes a single body design that avoids the challenges of soldering, welding, or otherwise attaching Nitinol wires 1908 to top hub 1904 and/or bushing 1906. FIG. 20 depicts an exemplary single body design in which wires 1908 are formed by removing material from Nitinol tubing. This design allowed the same collapsing and pitch-adjusting mechanism to be utilized, with minor changes to the test rig interface.

Figure 21:
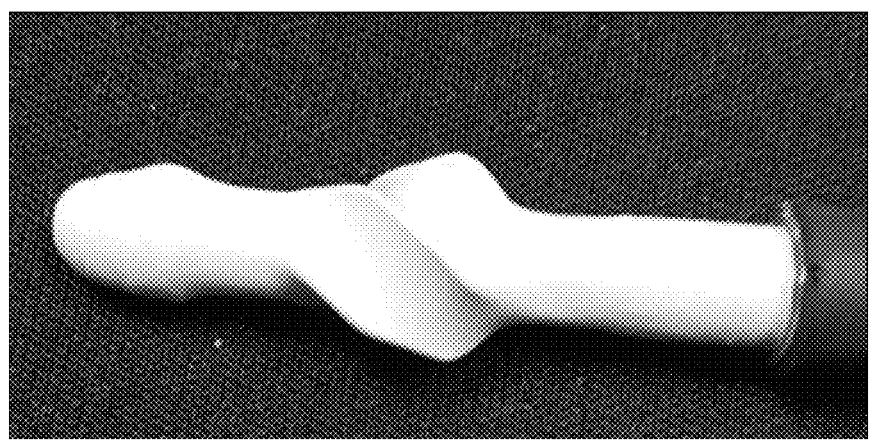
FIG. 21 depicts a single-body impeller covered with miniature latex balloons according to an embodiment of the invention.

Miniature latex balloons were used to cover the impeller. The resulting impeller is depicted in FIG. 21. Heat shrink tubing was used at the end to seal the balloon to prevent any leakage. This method gave the smoother finish desired.

MRI-Compatible Impellers and Pumps

The impellers and pumps described herein can be fabricated from non-ferrous materials in order to enable Magnetic Resonance Imaging (MRI) of subjects receiving the pumps. Such imaging can be utilized for a variety of medical reasons and is particularly useful in imaging blood flow around the impeller.

Exemplary non-ferrous materials include non-ferrous metals such as aluminum, cobalt, copper, nickel, tin, titanium, and zinc, as well as alloys thereof such as bronze, nickel-titanium (e.g., Nitinol). Other exemplary non-ferrous materials include fiberglass, graphite carbon, carbon fiber, carbon nanotube, ceramics, polyesters, aramids, para-aramids, meta-aramids, aromatic polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nylon, biosynthetic polymers, and blends of the same. For example, a drive shaft or flexible cable can be fabricated from a non-ferrous metal such as bronze and/or a polymer such as a para-aramid having sufficient stiffness to resist kinking during rotation of impeller in anatomic conditions.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A variable pitch impeller for a blood pump, the variable pitch impeller comprising:
a flexible polymer defining a plurality of helical blades and helical flutes extending from a first end to a second end, the plurality of helical blades having a resting non-zero blade pitch;
an external shaft coupled to the first end of the flexible polymer; and
an internal shaft received within the external shaft and coupled to the second end of the flexible polymer;
wherein the internal shaft and the external shaft are rotatable with respect to each other to achieve a second blade pitch of the plurality of helical blades different from the resting non-zero blade pitch, the second blade pitch between about 0.0001° and about 2,880°.

2. The variable pitch impeller of claim 1, wherein the plurality of helical blades consists of between 2 and 10 blades.

3. The variable pitch impeller of claim 1, wherein the plurality of helical blades are arranged at uniform angles about the impeller.

4. The variable pitch impeller of claim 3, further comprising:
one or more fixed blades.

5. The variable pitch impeller of claim 4, wherein the one or more fixed blades are located at an opposite end of the impeller from the plurality of helical blades.

6. The variable pitch impeller of claim 1, wherein the plurality of helical blades have a height between about 0.1 mm and about 15 mm.

7. The variable pitch impeller of claim 1, wherein the impeller has an external diameter between about 3 mm and about 28 mm.

8. The variable pitch impeller of claim 1, wherein the flexible polymer includes one or more polymers selected from the group consisting of: piezoelectric polymers and electroactive polymers.

9. The variable pitch impeller of claim 1, wherein the flexible polymer includes biocompatible polyurethane.

10. The variable pitch impeller of claim 1, wherein the flexible polymer is decouplable from the external shaft and the internal shaft.

11. The variable pitch impeller of claim 1, wherein the variable pitch impeller is fabricated entirely from non-ferrous materials.

12. The variable pitch impeller of claim 1, wherein the inner shaft is fabricated from a bronze alloy.

13. A blood pump comprising the variable pitch impeller as described in claim 1.

14. A variable pitch impeller for a blood pump, the variable pitch impeller comprising:
a flexible polymer defining a plurality of helical blades and helical flutes extending from a first end to a second end;
an external shaft coupled to the first end of the flexible polymer; and
an internal shaft received within the external shaft and coupled to the second end of the flexible polymer;
wherein the internal shaft and the external shaft are rotatable with respect to each other to achieve a blade pitch per length of the plurality of helical blades of at least 2.8°/mm.

15. The variable pitch impeller of claim 14, wherein the blade pitch per length of the plurality of helical blades is at least 8.0°/mm.

16. The variable pitch impeller of claim 14, wherein the blade pitch per length of the plurality of helical blades is at least 11.0°/mm.

* * * * *